US012629010B2

(12) United States Patent
Nakanishi

(10) Patent No.: US 12,629,010 B2
(45) Date of Patent: May 19, 2026

(54) ENDOSCOPE DEVICE AND CONNECTION DETERMINATION METHOD

(71) Applicant: Sony Olympus Medical Solutions Inc., Tokyo (JP)

(72) Inventor: Tatsuya Nakanishi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 518 days.

(21) Appl. No.: 18/161,097

(22) Filed: Jan. 30, 2023

(65) Prior Publication Data

US 2023/0255462 A1 Aug. 17, 2023

(30) Foreign Application Priority Data

Feb. 16, 2022 (JP) ................................. 2022-022495

(51) Int. Cl.
A61B 1/06 (2006.01)
A61B 1/00 (2006.01)
A61B 1/07 (2006.01)
(52) U.S. Cl.
CPC ........ A61B 1/0655 (2022.02); A61B 1/00009 (2013.01); A61B 1/00126 (2013.01); A61B 1/0638 (2013.01); A61B 1/07 (2013.01)
(58) Field of Classification Search
CPC .............. A61B 1/0655; A61B 1/00009; A61B 1/00126; A61B 1/0638; A61B 1/07; A61B 1/00057; A61B 1/00006; G02B 23/2469
See application file for complete search history.

(56) References Cited

U.S. PATENT DOCUMENTS

| | | | | |
|---|---|---|---|---|
| 4,782,386 A | * | 11/1988 | Ams | H05B 41/34 |
| | | | | 348/371 |
| 6,468,204 B2 | * | 10/2002 | Sendai | A61B 1/00009 |
| | | | | 600/118 |
| 6,511,422 B1 | * | 1/2003 | Chatenever | A61B 1/0661 |
| | | | | 600/180 |
| 2001/0056282 A1 | * | 12/2001 | Sonnenschein | A61B 1/0051 |
| | | | | 606/139 |

(Continued)

FOREIGN PATENT DOCUMENTS

| | | |
|---|---|---|
| CN | 112702942 A | 4/2021 |
| JP | S60234637 A | 11/1985 |

(Continued)

*Primary Examiner* — Anh Tuan T Nguyen
*Assistant Examiner* — Jae Woo
(74) *Attorney, Agent, or Firm* — XSENSUS LLP

(57) ABSTRACT

An endoscope device includes a light source that supplies first light having in a first emission pattern that changes with time and a second light that is at least partially superimposed on the first light and changes in a second emission pattern with time, an optical system including an insertion member, that illuminates a target region of a subject with light from the light source, a camera configured to receive reflected light reflected by the target region, and a control circuit. The control circuit is configured to detect whether reflected light of third light changing in a combined pattern obtained by combining the first emission pattern and the second emission pattern is received. When the reflected light of the third light is received, the control circuit is configured to determine that the light guide and the insertion member are connected.

21 Claims, 16 Drawing Sheets

(56) References Cited

U.S. PATENT DOCUMENTS

| | | | | |
|---|---|---|---|---|
| 2002/0013512 A1* | 1/2002 | Sendai | | A61B 5/0084 |
| | | | | 600/118 |
| 2004/0204645 A1* | 10/2004 | Saadat | | A61B 5/06 |
| | | | | 600/117 |
| 2006/0099548 A1* | 5/2006 | Rizoiu | | A61B 5/0088 |
| | | | | 433/29 |
| 2007/0088198 A1* | 4/2007 | Koitabashi | | A61B 1/00124 |
| | | | | 600/182 |
| 2008/0114224 A1* | 5/2008 | Bandy | | A61B 8/4236 |
| | | | | 600/459 |
| 2014/0031629 A1* | 1/2014 | Kamimura | | A61B 1/07 |
| | | | | 600/101 |
| 2014/0094649 A1* | 4/2014 | Ito | | A61B 1/0669 |
| | | | | 600/114 |
| 2016/0015471 A1* | 1/2016 | Piron | | A61B 1/045 |
| | | | | 600/424 |
| 2016/0206185 A1* | 7/2016 | Kinouchi | | A61B 1/00013 |
| 2017/0007097 A1* | 1/2017 | Takei | | A61B 1/07 |
| 2017/0099421 A1* | 4/2017 | Nakajima | | H04N 3/02 |
| 2018/0199798 A1* | 7/2018 | Kaneko | | G06T 3/60 |
| 2019/0058819 A1* | 2/2019 | Kobayashi | | G02B 23/2446 |
| 2019/0110660 A1* | 4/2019 | Rama Rao | | A61B 1/041 |
| 2020/0015925 A1* | 1/2020 | Scheib | | A61B 1/07 |
| 2020/0085285 A1* | 3/2020 | Yamada | | A61B 1/00057 |
| 2020/0245855 A1* | 8/2020 | Tamura | | A61B 1/00119 |
| 2020/0322598 A1* | 10/2020 | Niwa | | A61B 1/00059 |
| 2022/0061633 A1* | 3/2022 | Shang | | A61B 1/0056 |
| 2022/0378284 A1* | 12/2022 | Tabata | | A61B 1/0669 |
| 2023/0284880 A1* | 9/2023 | Niwa | | A61B 1/07 |
| 2023/0284890 A1* | 9/2023 | Niwa | | A61B 1/0655 |
| 2025/0017453 A1* | 1/2025 | Talbot | | G01J 3/28 |

FOREIGN PATENT DOCUMENTS

| JP | S63155984 A | 6/1988 |
|---|---|---|
| JP | H05133839 A | 5/1993 |
| JP | H05248950 A | 9/1993 |
| JP | 2001321338 A | 11/2001 |
| JP | 2004033755 A | 2/2004 |
| JP | 2009153899 A | 7/2009 |
| JP | 2010-82041 A | 4/2010 |
| JP | 2013017819 A | 1/2013 |

* cited by examiner

*FIG. 14*

ENDOSCOPE DEVICE AND CONNECTION DETERMINATION METHOD

CROSS REFERENCE TO RELATED APPLICATIONS

This application claims the benefit of Japanese Priority Patent Application JP 2022-022495 filed on Feb. 16, 2022, the entire contents of which are incorporated herein by reference.

TECHNICAL FIELD

The present disclosure relates to an endoscope device and a connection determination method.

BACKGROUND ART

In the medical field, an endoscope device is used to observe a subject. In an endoscope device, illumination light generated by a light source device is guided to the inside of the endoscope via a light guide. The illumination light guided into the endoscope travels inside the endoscope and is emitted from the distal end of the endoscope into the living body.

In an endoscope device of a type in which a light guide and an endoscope are detachably connected, a light amount generated in a light source device is limited so as to ensure safety even when illumination light is emitted from the light source device in a state in which the endoscope is not connected to the light guide.

However, in order to enhance the visibility of the endoscopic image, it is preferable to increase the amount of light generated by the light source device while keeping the amount of light emitted from the distal end of the endoscope within a safe range.

PTL 1 below discloses an invention in which whether or not a distal end of an endoscope is inserted into a living body is detected based on a pressure change, and illumination light is generated in a light source device only in a case where the distal end of the endoscope is inserted into the living body. However, in the present invention, since the illumination light is generated even in a state where the endoscope is not connected to the light guide, it is necessary to limit the amount of light generated in the light source device.

CITATION LIST

Patent Literature

[PTL 1]
JP 2010-82041A

SUMMARY

Technical Problem

The present disclosure is to solve the above problem, and provides an endoscope device and a connection determination method that prevent light emission exceeding an allowable amount from being performed in a state where an endoscope is not connected to a light guide.

Solution to Problem

An endoscope device according to the present disclosure includes: a light source unit configured to supply light to one end of a light guide; an insertion member including a connecting portion detachably connected to the other end of the light guide and a distal end that emits the light from the light guide to a target region of a subject; a light receiving unit configured to receive reflected light reflected by the target region of the subject and incident from the distal end; and a control unit configured to determine a connection state between the light guide and the insertion member on the basis of information of the reflected light received by the light receiving unit.

BRIEF DESCRIPTION OF DRAWINGS

FIG. 14 is a diagram illustrating an internal configuration of an insertion member and a camera head in an endoscope device according to the fourth embodiment.

DESCRIPTION OF EMBODIMENTS

Figure 1:
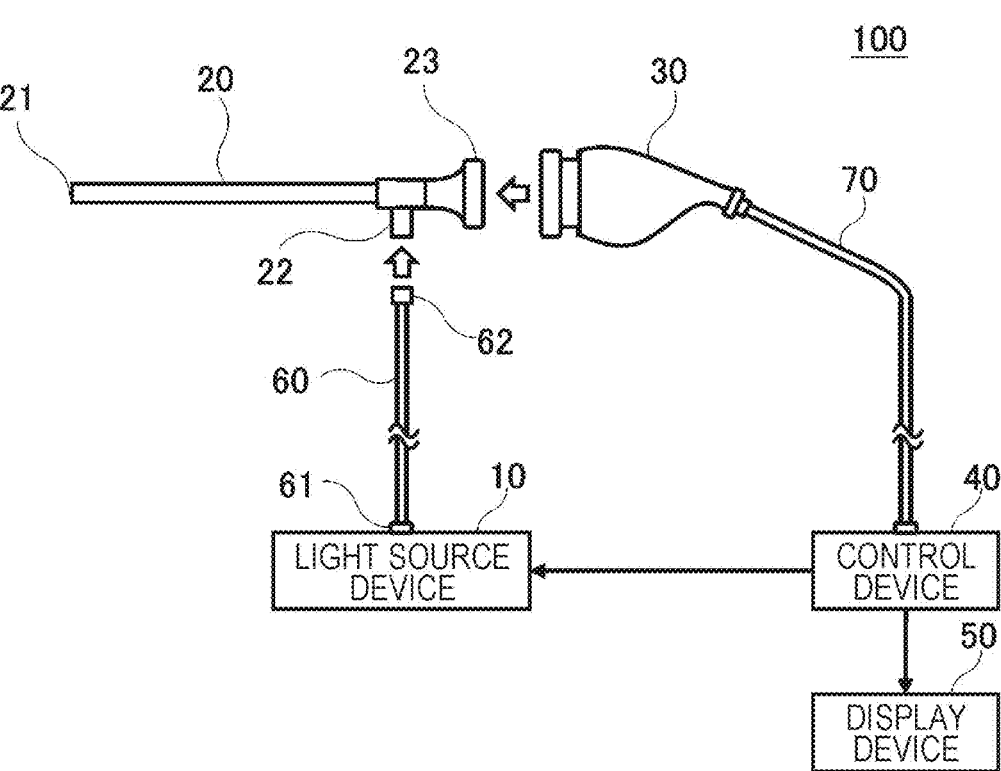
FIG. 1 is a diagram illustrating a configuration of an endoscope device according to a first embodiment.

Hereinafter, embodiments of the present disclosure will be described with reference to the drawings. In the drawings, the same or corresponding elements are denoted by the same reference numerals, and detailed description thereof is omitted as appropriate.

First Embodiment

FIG. 1 is a diagram illustrating a configuration of an endoscope device 100 according to a first embodiment of the present disclosure. The endoscope device 100 is used in the medical field and is a device for imaging or observing a target region (observation target) in a living body to be a subject. The endoscope device 100 includes a light source device 10, an insertion member 20 (endoscope main body), a camera head 30, a control device 40, a display device 50, a light guide 60, and a transmission cable 70.

The light source device 10 is a light source unit that generates light for irradiating the inside of the living body. The light generated by the light source device 10 includes light for observation of the inside of the living body (illumination light) and light for determining a connection state between the light guide 60 and the insertion member 20 (test light). The light source device 10 is detachably connected to one end 61 (connector) of the light guide 60, and supplies the generated light to one end 61 of the light guide 60. The other end 62 (connector) of the light guide 60 is detachably connected to the connecting portion 22 of the insertion member 20. The connecting portion 22 detachably connects the other end 62 of the light guide 60 to the internal space of the insertion member 20. The internal space of the insertion member 20 is a space through which light can propagate. The insertion member 20 includes a rigid endoscope having a rigid and elongated shape, and can be inserted into the living body from the distal end 21. The proximal end 23 (eyepiece portion) of the insertion member 20 is detachably connected to the camera head 30. The light guide 60 is an optical cable that guides light supplied from the light source device 10 to the insertion member 20. The light guided from the light guide 60 is guided to the internal space of the insertion member 20 via the connecting portion 22, and travels while being attenuated toward the distal end 21 of the insertion member 20.

Figure 2:
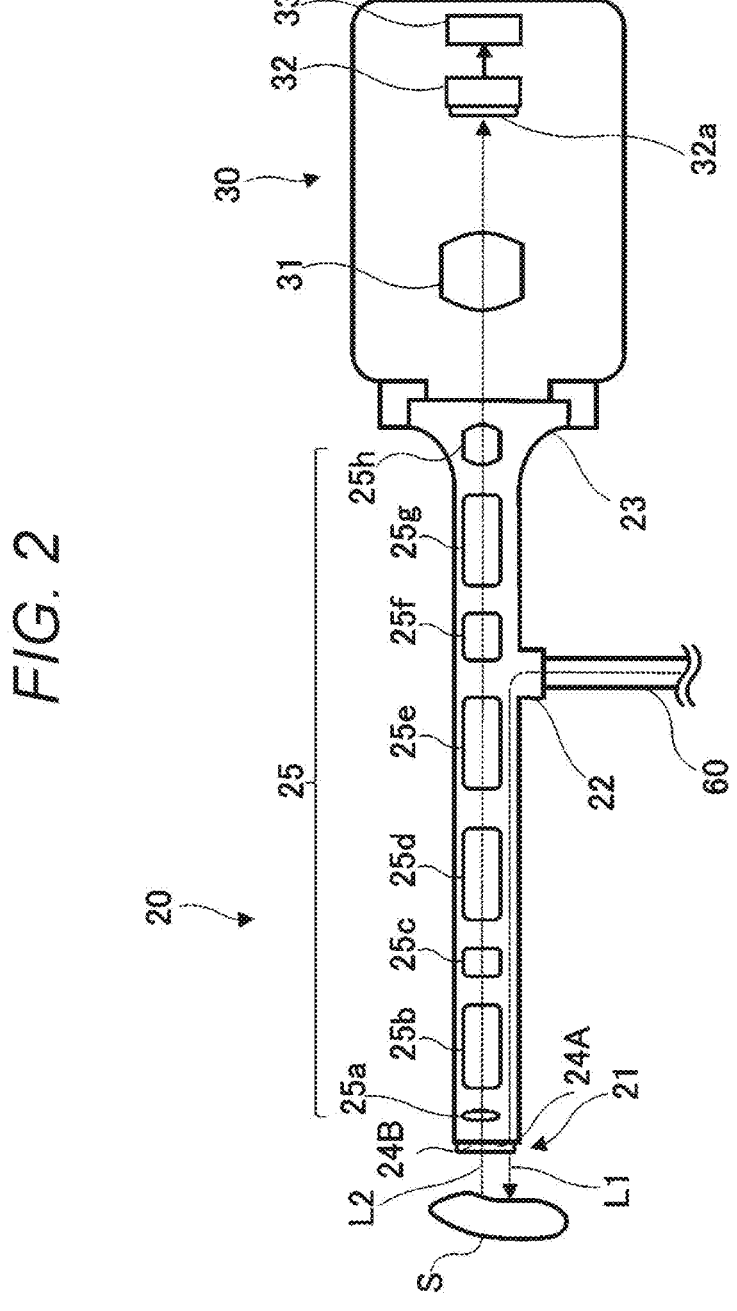
FIG. 2 is a diagram illustrating an internal configuration of an endoscope and a camera head.

FIG. 2 is a diagram illustrating an internal configuration of the insertion member 20 and the camera head 30. The distal end 21 of the insertion member 20 is provided with an emission unit 24A that emits light supplied from the light source device 10 via the light guide 60 toward a target region (observation target S) in the subject (living body). The emission unit 24A may include a lens or another member, or may be a space (hole). The light L1 (Illumination light, test light, or superimposed light thereof) emitted from the emission unit 24A is reflected by the observation target S in the living body. The distal end 21 of the insertion member 20 is provided with an incident portion 24B on which a reflected wave is incident. The incident portion 24B may include a lens or another member, or may be a space (hole). The reflected light enters the incident portion 24B and is guided again into the insertion member 20. Although the emission unit 24A and the incident portion 24B are provided separately, the emission unit 24A and the incident portion 24B may be the same. An observation optical system 25 including optical lenses 25a, 25b, 25c, 25d, 25e, 25f, 25g, and 25h is provided inside the insertion member 20. The reflected light L2 from the observation target S is collected by the observation optical system 25 and guided to the camera head 30 via the proximal end 23 of the insertion member 20.

A lens unit 31, an imaging unit 32, and a communication unit 33 are provided inside the camera head 30. The imaging unit 32 corresponds to a light receiving unit that receives reflected light from the observation target S. The optical axes of the lens unit 31 and the imaging unit 32 coincide with the optical axis of the observation optical system 25 of the insertion member 20. The reflected light L2 guided to the camera head 30 is condensed by the lens unit 31 and forms an image on the imaging element 32a of the imaging unit 32 by exposure. The imaging unit 32 images the observation target formed on the imaging element 32a at a predetermined frame rate and converts the observation target into an electrical signal. As a result, an image signal of the observation target S is generated. The communication unit 33 transmits the image signal to the control device 40 via the transmission cable 70.

One end of the transmission cable 70 in FIG. 1 is detachably connected to the control device 40, and the other end is detachably connected to the camera head 30. The transmission cable 70 transmits an image signal and the like output from the camera head 30 to the control device 40, and transmits a control signal, a synchronization signal, a clock, power, and the like output from the control device 40 to the camera head 30. As the transmission cable 70, a communication cable (for example, a cable for high-speed serial transmission) such as a coaxial cable or an optical fiber cable can be used. Transmission of an image signal or the like from the camera head 30 to the control device 40 via the transmission cable 70 may be transmission by an optical signal or transmission by an electric signal. In addition, an image signal may be transmitted as an optical signal and a control signal may be transmitted as an electrical signal by using both the optical signal and the electrical signal. Similarly, a control signal, a synchronization signal, and a clock can be transmitted from the control device 40 to the camera head 30 via the transmission cable 70, either by an optical signal or by an electric signal. Wireless transmission may be used instead of wired transmission. In this case, signals can be transmitted using a system or standard such as a wireless local area network (LAN), Bluetooth (registered trademark), or infrared communication.

Figure 3:
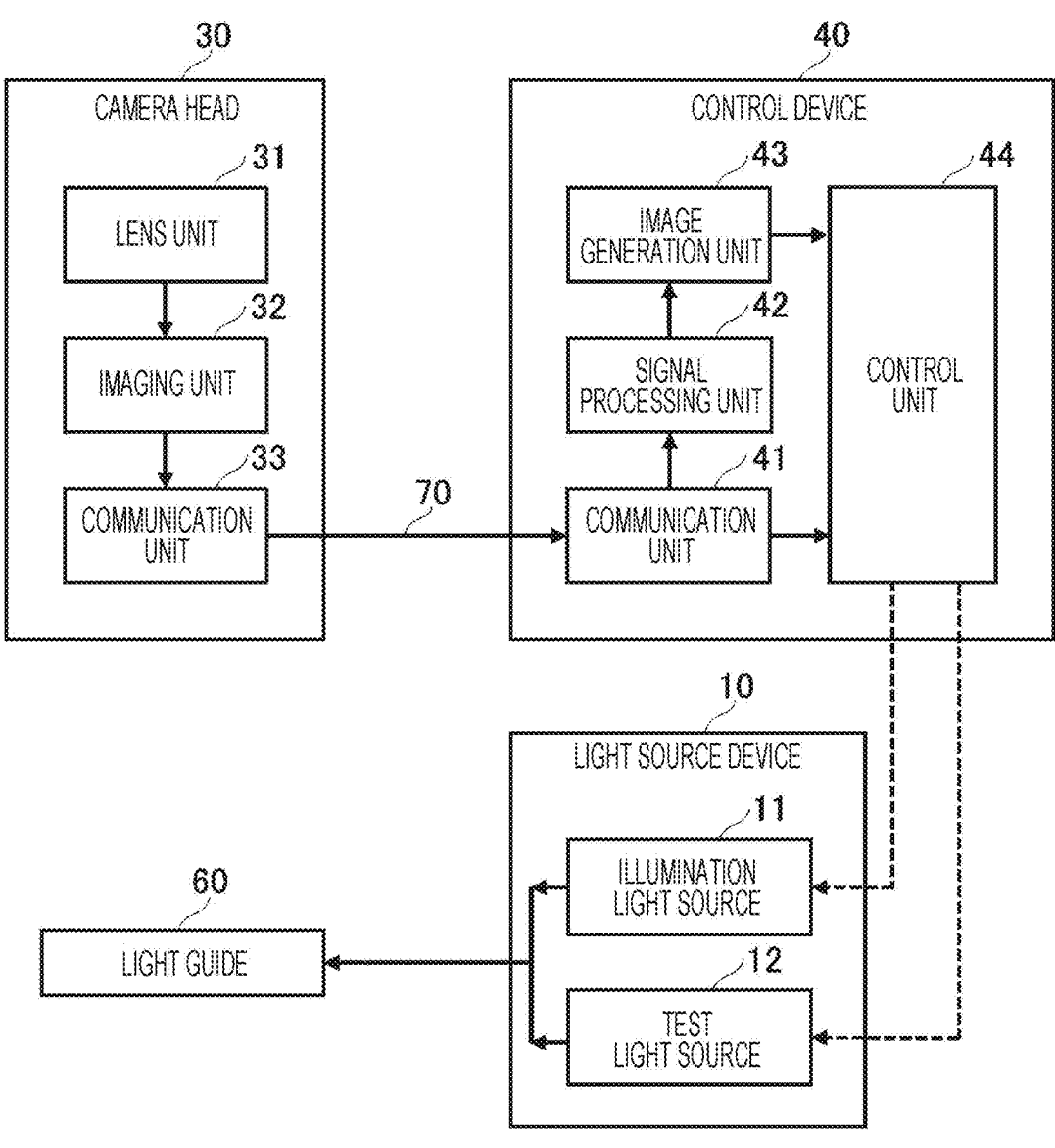
FIG. 3 is a detailed block diagram of a light source device, a camera head, and a control device included in the endoscope device according to the first embodiment.

In FIG. 1, the control device 40 controls the entire operation of the endoscope device 100 such as the light source device 10, the camera head 30, and the display device 50. The control device 40 generates an image signal (video signal) for display by performing various types of image processing on the image signal of the observation target S received from the camera head 30 via the transmission cable 70. The control device 40 outputs the video signal to the display device 50, and the display device 50 displays the image of the observation target S on the basis of the video signal. The display device 50 is, for example, a display device such as a liquid crystal display or an organic electroluminescence (EL) display. The display device 50 may display information other than the image of the observation target S, for example, a screen of an application for image display. The control device 40 may transmit the video signal through a transmission cable or wirelessly. FIG. 3 is a detailed block diagram of the light source device 10, the camera head 30, and the control device 40 included in the endoscope device 100. In the block diagram of FIG. 3, only blocks of functions related to the technology according to the present disclosure are illustrated, and illustration of blocks of other functions is omitted.

The light source device 10 includes an illumination light source 11 and a test light source 12. The light source included in the light source device 10 is not limited to the illumination light source 11 and the test light source 12, and the light source device 10 may further include another light source.

The illumination light source 11 irradiates the inside of the living body and generates light (illumination light) for observing the observation target S. The illumination light is, for example, visible light, infrared rays for excitation observation, ultraviolet rays, or the like. The wavelength of the illumination light is not limited to a specific value or range. The illumination light may be laser light. As an example, the illumination light source 11 includes a halogen lamp, a xenon lamp, a light emitting diode (LED), a laser diode (LD), or the like. The illumination light source 11 is controlled by the control device 40.

The test light source 12 generates light (test light) for determining a connection state between the light guide 60 and the insertion member 20. The test light may be visible light, infrared light, ultraviolet light, or the like. The wavelength of the test light is not limited to a specific value or range. The test light may be a laser beam or the like. As an example, the test light source 12 includes a halogen lamp, a xenon lamp, a light emitting diode (LED), a laser diode (LD), or the like. The test light source 12 is controlled by the control device 40. The type of the test light source 12 may be the same as or different from that of the illumination light source 11. The wavelength range of the test light source 12 may be the same or at least partially the same as the illumination light source 11. The illumination light emitted by the test light source 12 corresponds to the first light emitted by the light source device 10, and the illumination light emitted by the illumination light source 11 corresponds to the second light emitted by the light source device 10.

The illumination light source 11 emits pulsed light at a frequency fa, and the test light source 12 is controlled by the control device 40 to emit pulsed light at a frequency fb. That is, the pulse frequency of the illumination light source 11 is fa, and the pulse frequency of the test light source 12 is fb. The frequency fb is higher than the frequency fa, for example. For example, fb is an integer multiple of fa. The illumination light source 11 and the test light source 12 are synchronized with each other, and the illumination light and the test light are simultaneously emitted at a cycle corresponding to the frequency fa. In a period other than the period in which the light beams are simultaneously emitted, only the test light is emitted, or neither the test light nor the illumination light is emitted.

The illumination light generated by the illumination light source 11 and the test light generated by the test light source 12 are supplied to one end 61 of the light guide 60. When the illumination light source 11 and the test light source 12 simultaneously emit light, superimposed light in which the illumination light and the test light are superimposed is supplied to one end 61 of the light guide 60.

In FIG. 3, the camera head 30 includes a lens unit 31, an imaging unit 32, and a communication unit 33.

The lens unit 31 is configured using one or a plurality of optical lenses. The lens unit 31 condenses reflected light from the observation target S guided into the camera head 30 and forms an image on an imaging element 32*a* of the imaging unit 32 by exposure. The lens unit 31 is configured to be slidable along the optical axis. As the lens unit 31 slides along the optical axis, an optical zoom mechanism that changes the angle of view, a focus mechanism that changes the focal position, and the like are realized.

The imaging unit 32 images an image of the observation target S formed on the imaging element 32*a* at a predetermined frame rate and converts the image into an electric signal, thereby generating an image signal of the observation target S. As an example, the imaging element 32*a* includes a charge coupled device (CCD) image sensor, a complementary metal oxide semiconductor (CMOS) image sensor, or the like. The imaging unit 32 corresponds to a light receiving unit that receives reflected light from the observation target S.

The communication unit 33 transmits the image signal of the observation target S for each frame generated by the imaging unit 32 to the control device 40 via the transmission cable 70.

The imaging unit 32 and the communication unit 33 may be realized by a general-purpose processor such as a central processing unit (CPU), a micro processing unit (MPU), or a graphics processing unit (GPU), or may be realized by an integrated circuit such as an application specific integrated circuit (ASIC) or a field programmable gate array (FPGA). In a case where the imaging unit 32 and the communication unit 33 are configured by a general-purpose processor, the functions of the imaging unit 32 and the communication unit 33 are realized by causing the general-purpose processor to execute software or a program.

The control device 40 includes a communication unit 41, a signal processing unit 42, an image generation unit 43, and a control unit 44.

The communication unit 41 receives the image signal of the observation target S for each frame transmitted from the camera head 30 via the transmission cable 70. The signal processing unit 42 generates a digitized image signal by performing A/D conversion, noise removal, and the like on the image signal of the observation target S received by the communication unit 41.

The image generation unit 43 performs various types of image processing such as interpolation, color correction, color enhancement, and contour enhancement on the digitized image signal. The image signal (video signal) after the image processing is transmitted to the display device 50 (see FIG. 1), and an image based on the video signal is displayed by the display device 50.

The control unit 44 controls operation of each unit included in the control device 40. In addition, the control unit 44 controls the operations of the illumination light source 11 and the test light source 12 included in the light source device 10 by transmitting a control signal to the light source device 10.

Furthermore, the control unit 44 performs processing of determining a connection state as to whether or not the light guide 60 and the insertion member 20 are connected on the basis of the image signal for each frame (details will be described later). As long as the image signal used in this processing is based on the image signal acquired by the imaging unit 32, the image signal may be an image signal after A/D conversion or noise removal, an image signal subjected to image processing by the image generation unit 43, or an image signal generated during image processing by the image generation unit 43.

The communication unit 41, the signal processing unit 42, the image generation unit 43, and the control unit 44 may be realized by a general-purpose processor such as a CPU, an MPU, or a GPU, or may be realized by an integrated circuit such as an ASIC or an FPGA. In a case where the communication unit 41, the signal processing unit 42, the image generation unit 43, and the control unit 44 are configured by a general-purpose processor, the functions of the communication unit 41, the signal processing unit 42, the image generation unit 43, and the control unit 44 are realized by causing the general-purpose processor to execute software or a program.

Next, determination processing for determining the connection state between the light guide 60 and the insertion member 20 performed by the control device 40 in the endoscope device 100 will be described with reference to FIGS. 4 and 5.

Figure 4:
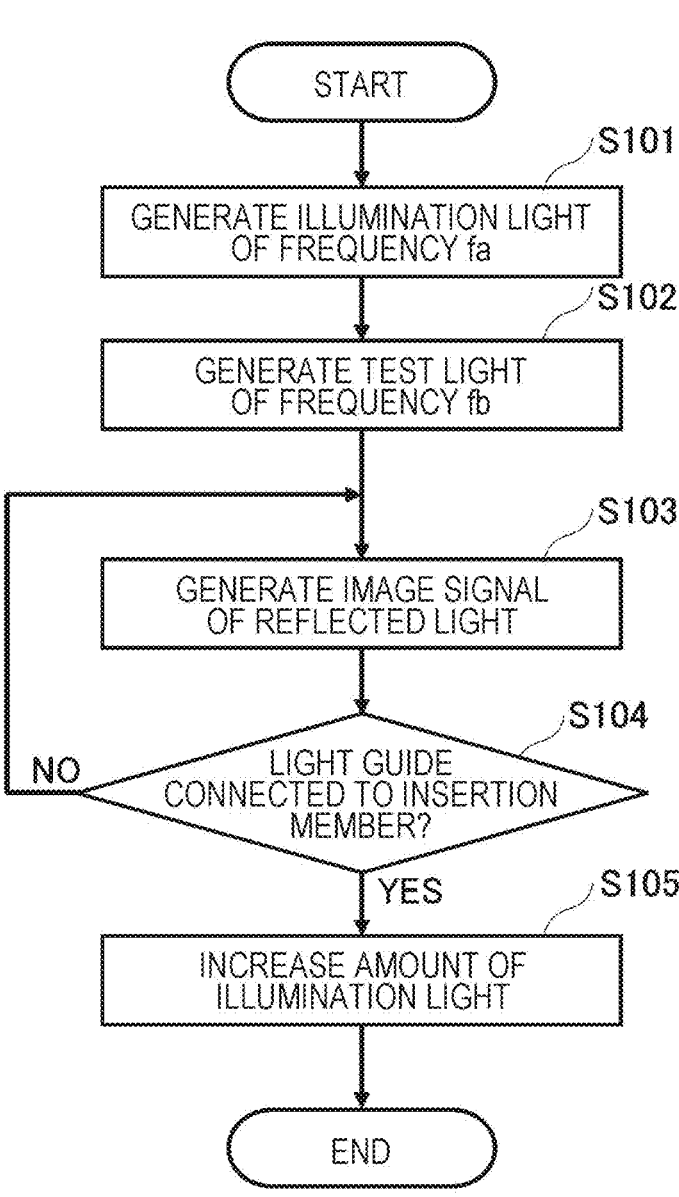
FIG. 4 is a flowchart illustrating determination processing of a connection state between a light guide and an insertion member in the endoscope device according to the first embodiment.

FIG. 4 is a flowchart of an example of determination processing of a connection state between the light guide 60 and the insertion member 20 according to the first embodiment.

In step S101, the control unit 44 of the control device 40 generates pulsed illumination light blinking at the frequency fa from the illumination light source 11 of the light source device 10. Blinking of the illumination light at the frequency fa means that the illumination light repeats light emission and non-light emission at a time interval (second time interval) corresponding to the frequency fa. That is, the emission pattern of the illumination light is a pattern in which the amplitude changes with time at the frequency fa. The frequency fa is, for example, 60 Hz. However, the frequency fa of the illumination light is not limited to 60 Hz, and may be any other frequency.

Figure 5A:
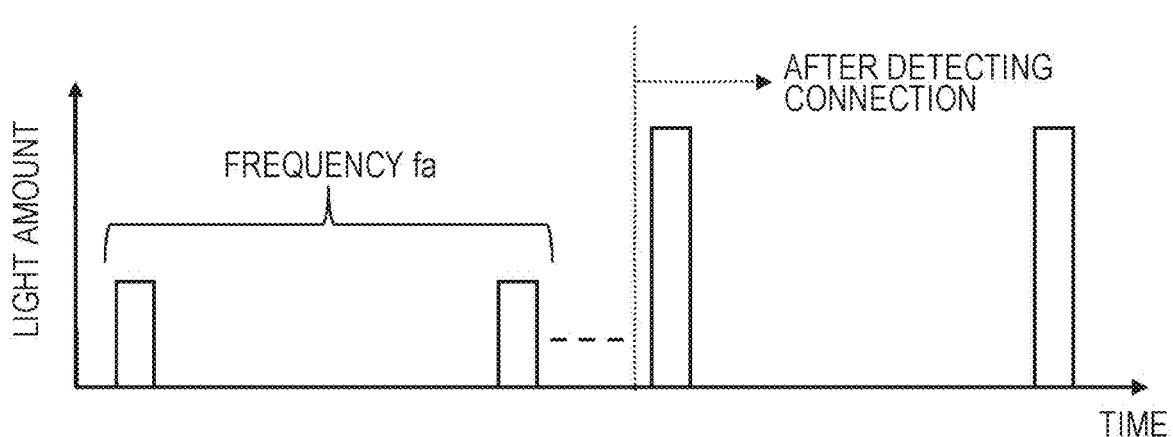
FIG. 5A is a view illustrating an example of illumination light, test light (FIG. 5B), and superimposed light (FIG. 5C) thereof according to the first embodiment.

The left side of FIG. 5(A) illustrates an example of the illumination light blinking (pulse lighting) at the frequency fa generated by the illumination light source 11 before the connection between the light guide 60 and the insertion member 20 is detected. In this example, the frequency fa is 60 Hz.

In step S102, the control unit 44 of the control device 40 generates pulsed test light blinking at the frequency fb from the test light source 12 of the light source device 10. The blinking of the test light at the frequency fb means that the test light repeats light emission and non-light emission at a time interval (first time interval) corresponding to the frequency fb. That is, the emission pattern of the test light is a pattern in which the amplitude changes with time at the frequency fb. Step S102 may be executed simultaneously with step S101. The frequency fb of the test light is different from the frequency fa of the illumination light. The frequency fb is an integer multiple of the frequency fa and is higher than the frequency fa of the illumination light. The frequency fb is, for example, 300 Hz. The frequency fb of the test light is not limited to 300 Hz. It is not excluded that the frequency f2 of the test light is lower than the frequency f1 of the illumination light, and that the frequency fb of the test light is the same as the frequency fa of the illumination light. In order not to hinder a user such as a physician from observing the inside of the living body through the display device 50, the frequency fb of the test light is preferably a high frequency that is imperceptible by human perception. Furthermore, in a case where the ambient light that periodically blinks like a fluorescent lamp may be mixed into the insertion member 20 (insertion member), the frequency of the test light is preferably a value distinguishable from the frequency of the ambient light (for example, a frequency higher or lower than the frequency of the ambient light).

The emission pattern of the test light corresponds to a first emission pattern in which light emission changes with time in the test light source 12, and the emission pattern of the illumination light corresponds to a second emission pattern in which light emission changes with time in the illumination light source 11. The test light changing in the first emission pattern corresponds to the first light, and the illumination light changing in the second emission pattern corresponds to the second light. A pattern obtained by combining the emission pattern (first emission pattern) of the test light and the emission pattern (second emission pattern) of the illumination light is referred to as a combined pattern. The light changing in the combined pattern corresponds to the third light in which the first light emitting in the first emission pattern and the second light emitting in the second emission pattern are superimposed. That is, the third light changes in the emission pattern obtained by combining the first emission pattern and the second emission pattern. In the present embodiment, the combined pattern is used as a pattern (hereinafter, referred to as a connection determination pattern) for determining whether the light guide 60 is connected to the insertion member 20.

Figure 5B:
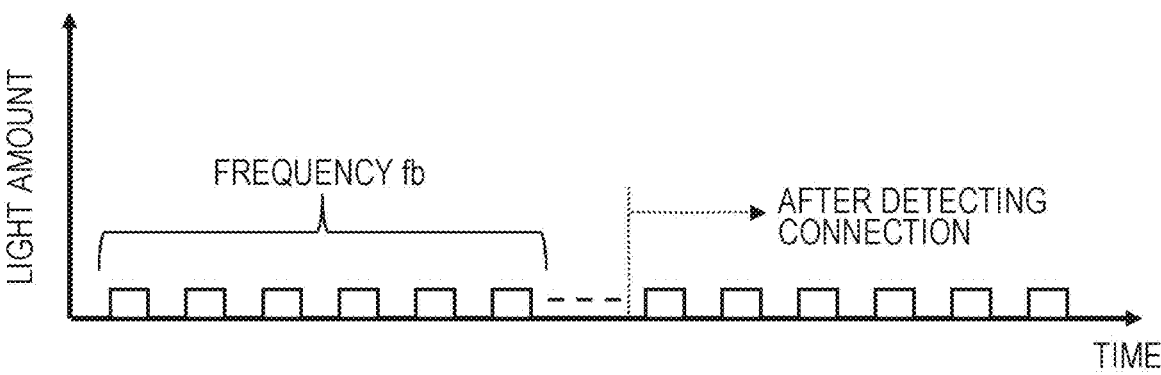

An example of the test light blinking (pulse lighting) at the frequency fb generated by the test light source 12 before the detection of the connection between the light guide 60 and the insertion member 20 is illustrated on the left side of FIG. 5(B). In this example, the frequency fb is 300 Hz, which is 5 times the blinking frequency fa of the illumination light. The pulse width of the test light is assumed to be the same as the pulse width of the illumination light. The light amount of the test light is smaller than the light amount of the illumination light.

The light amount in a case where the illumination light source 11 and the test light source 12 simultaneously emit light, that is, the total light amount of the illumination light and the test light is suppressed to a light amount (allowable amount) that ensures safety even when light is emitted from the other end 62 of the light guide 60 in a state where the other end 62 is not connected to the insertion member 20.

In addition, the illumination light and the test light are controlled by the control device 40 to blink (pulse light emission) at synchronized timing. That is, when the illumination light blinks at 60 Hz and the test light blinks at 300 Hz, after the illumination light and the test light are simultaneously turned on, only the test light is turned on 4 times. Then, the illumination light and the test light are simultaneously turned on again at the next timing. Thereafter, this operation is repeated. Therefore, the light supplied from the light source device 10 to the one end 61 of the light guide 60 is only the light in which the illumination light and the test light are superimposed in the case of the simultaneous lighting, and only the test light in the case other than the simultaneous lighting.

Figure 5C:
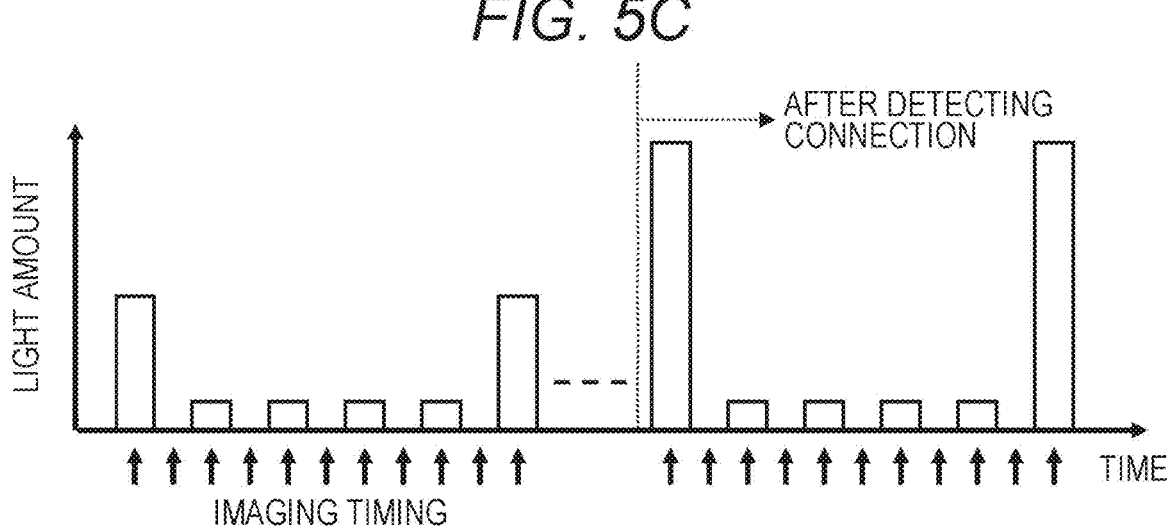

An example of light supplied from the light source device 10 (Illumination light source 11, test light source 12) to one end 61 of the light guide 60 before detection of connection between the light guide 60 and the insertion member 20 is illustrated on the left side of FIG. 5(C). The light supplied to one end 61 of the light guide 60 is light (superimposed light) obtained by adding the light on the left side in FIG. 5(A) and the light on the left side in FIG. 5(B) at the same time. During a period in which the illumination light and the test light are simultaneously turned on, the illumination light and the test light are superimposed, and the superimposed light is supplied to one end 61. By superimposing the illumination light and the test light, the light amount supplied to the one end 61 is larger than the illumination light and the test light. During a period other than the synchronous lighting period, only the test light is intermittently supplied to the one end 61 (at the frequency fb). In this example, the pulse width of the test light and the pulse width of the illumination light are the same, and when the test light and the illumination light are simultaneously turned on, the start time and the end time of the pulse of each of the test light and the illumination light coincide with each other. Note that the synchronization timing of the illumination light and the test light may be arbitrary, and depending on the timing, only the illumination light may be supplied to the one end 61 of the light guide 60. The light supplied to one end 61 of the light guide 60 propagates in the light guide 60, and is guided from the connecting portion 22 of the insertion member 20 to the inside of the insertion member 20 via the other end 62 of the light guide 60. The light guided into the insertion member 20 travels while attenuating toward the distal end 21 of the insertion member 20, and is emitted from the distal end 21 (emission unit 24A) of the insertion member 20 toward the observation target S in the living body. Reflected light from the observation target S enters the inside of the insertion member 20 again from the distal end 21 (incident portion 24B), and is guided to the camera head 30 via the observation optical system 25.

In step S103 of FIG. 4, the imaging unit 32 of the camera head 30 images the reflected light from the observation target S at a frame rate (for example, 600 Hz) that is twice or more the frequency fb and converts the reflected light into an electric signal. As a result, the imaging unit 32 generates an image signal of, for example, 600 frames per second. At this time, the control unit 44 of the control device 40 synchronizes the imaging timing of the imaging unit 32 with the blinking timing of the test light (see FIG. 5(C)). As a result, imaging is performed at each of the timing of the reflected light of the superimposed light in which the illumination light and the test light are superimposed, the timing of the reflected light of the test light, and the timing at which neither the test light nor the illumination light is emitted.

In step S104, the control unit 44 of the control device 40 determines whether or not the other end 62 of the light guide 60 is connected to the insertion member 20 based on the image signal for each frame generated by the imaging unit 32.

Specifically, on the basis of the image signal for each frame, the control unit 44 performs processing of detecting whether reflected light of light having the above-described connection determination pattern (in the present embodiment, a combined pattern of the emission pattern of the test light and the emission pattern of the illumination light) is received. When detecting that the reflected light of the light changing in the connection determination pattern is received, the control unit 44 determines that the other end 62 of the light guide 60 is connected to the insertion member 20. When detecting that the reflected light of the light changing in the connection determination pattern is not received, the control unit 44 determines that the other end 62 of the light guide 60 is not connected to the insertion member 20.

An example of a method for detecting whether reflected light of light changing in a connection determination pattern is received will be described. A period (connection determination period) for determination is set, and luminance information of an image signal is measured for each frame during at least a part of the connection determination period. The measured luminance information is compared with two threshold values (set lower limit A_1 and upper limit A_2) for detecting the reflected light of the test light and two threshold values (lower limit B_1 and upper limit B_2) for detecting the reflected light of the superimposed light in which the illumination light and the test light are superimposed.

When the luminance information is greater than or equal to the lower limit A_1 and less than or equal to the upper limit A_2, the control unit 44 detects that the test light is received and sets the detection result as A. When the luminance information is greater than or equal to the lower limit B_1 and less than or equal to the upper limit B_2, the control unit 44 detects that the superimposed light is received and sets the detection result as a detection result B. In a case where the luminance information is less than the lower limit A_1 or greater than the upper limit A_2 and less than the lower limit B_1, the control unit 44 detects that neither the test light nor the superimposed light is received, and sets the detection result as a detection result X. When the luminance information is larger than the upper limit B_2, the luminance information may be treated as the detection result B or the detection result X.

The control unit 44 generates a sequence of detection results (detection result sequence) in which the detection results are arranged in time order of frames. The control unit 44 determines whether the unit sequence, which is the minimum unit of repetition of the detection result to be obtained according to the connection determination pattern, has been obtained a predetermined number of times (the predetermined number of times is one or a plurality of times) or more. In a case where the unit sequence is obtained a predetermined number of times or more, the control unit 44 detects that reflected light of light changing in the connection determination pattern is received. In the light emission example illustrated in FIG. 5(C), since a sequence of B, X, A, X, A, X, A, X, A, X should be obtained as a detection result per cycle corresponding to the frequency fa, the unit sequence is B, X, A, X, A, X, A, X, A, X. In a case where the unit sequence is included in the detection result sequence a predetermined number of times (the predetermined number is one or a plurality of times) or more according to the length of the connection determination period, the control unit 44 detects that reflected light of light changing in the connection determination pattern is received. In this case, the control unit 44 determines that the other end 62 of the light guide 60 is connected to the insertion member 20.

On the other hand, in a case where the unit sequence is not included in the detection result sequence the predetermined number of times or more, the control unit 44 detects that the reflected light of the light changing in the connection determination pattern is not received. In this case, the control unit 44 determines that the other end 62 of the light guide 60 is not connected to the insertion member 20.

The method of detecting whether the reflected light of the light changing in the connection determination pattern is received may be appropriately changed according to the frame rate of the imaging unit 32, the frequency of the illumination light, the frequency of the test light, and the like. For example, when the frame rate is doubled, the unit sequence in the example of FIG. 5(C) is B, B, X, X, A, A, X, X, A, A, A, X, A, X, A, A, X, X, A, A, A, X, X since each element of the unit sequence is continuously repeated twice.

An example of the luminance information of the image signal in one frame is average luminance of the image signal in one frame. In addition, values such as minimum luminance, center luminance, and maximum luminance may be used. The threshold value (lower limit and upper limit) of the test light is only required to be any value as long as the light amount of the reflected light of the test light can be detected. As an example, only the test light is emitted in advance to image the reflected light, and the minimum luminance and the maximum luminance of the image signal in one frame are calculated a plurality of times. Imaging may be performed on a plurality of observation targets. The plurality of observation targets may be different regions of the same subject, or may be one or more regions of different subjects. An upper limit reference value such as the calculated maximum value or average value of the maximum luminance, or a value obtained by adding a constant value (margin value) to the upper limit reference value is set as the upper limit. Similarly, a lower limit reference value such as the calculated minimum value or average value of the minimum luminance, or a value obtained by subtracting a certain value (margin value) from the lower limit reference value is set as the lower limit.

Alternatively, the threshold value may be determined from the information based on the light amounts of the illumination light and the test light and the information based on the characteristics of the observation target S on the basis of knowledge of the user such as a physician or an expert of image processing. The threshold value may be determined by other methods.

The threshold values (the lower limit and the upper limit) of the superimposed light can be similarly determined. The threshold value (lower limit and upper limit) of the superimposed light is only required to be any value as long as the light amount of the reflected light of the superimposed light can be detected. As an example, the test light and the illumination light are caused to simultaneously emit in advance, and the reflected light of the superimposed light is imaged, and the minimum luminance and the maximum luminance of the image signal in one frame are calculated a plurality of times. Imaging may be performed on a plurality of observation targets. The plurality of observation targets may be different regions of the same subject or regions of different subjects. An upper limit reference value such as the calculated maximum value or average value of the plurality of maximum luminance values, or a value obtained by adding a constant value (margin value) to the upper limit reference value is set as the upper limit. Similarly, a lower limit reference value such as a minimum value or an average value of the plurality of calculated minimum luminance values, or a value obtained by subtracting a certain value (margin value) from the lower limit reference value is set as the lower limit. Alternatively, the threshold value may be determined from the information based on the light amounts of the illumination light and the test light and the information based on the characteristics of the observation target S on the basis of knowledge of the user such as a physician or an expert of image processing. The threshold value may be determined by other methods.

In order to prevent the ambient light from being erroneously detected as the reflected light of the test light, the test light may have a light amount larger than that of the assumed ambient light. By using the threshold value determined in this manner, reflected light of light changing in the connection determination pattern can be appropriately detected.

The connection determination period may be determined by, for example, the number of frames or a time length from the start of the connection determination process. The start time point may be a timing at which the processing of this flowchart is started, or may be another arbitrarily determined timing. When the number of frames in the connection determination period is N (N is an integer of 2 or more, for example), the luminance information is compared with two threshold values for N frames. When the time length is M, the luminance information is compared with the threshold value for each frame during the time length M.

Note that the imaged image acquired by the imaging unit 32 may be displayed on the display device 50 even during the connection determination period.

In a case where it is determined in step S104 described above that the other end 62 of the light guide 60 is connected to the insertion member 20, in step S105, the control unit 44 increases the amount of illumination light generated by the illumination light source 11 of the light source device 10. Since the other end 62 of the light guide 60 is connected to the insertion member 20, light is prevented from leaking from the other end 62 of the light guide 60. Therefore, the amount of illumination light can be increased to the extent that the amount of light emitted from the distal end 21 (emission unit 24A) of the insertion member 20 to the observation target S falls within a safe range (allowable amount). Specifically, a value (target value) of the light amount may be determined in advance, and the control unit 44 may increase the light amount of the illumination light up to the target value.

Alternatively, an increase width of the light amount may be determined in advance, and the control unit 44 may increase the light amount of the illumination light by the increase width.

After increasing the light emission amount of the illumination light source 11 or after detecting the connection, the control unit 44 may continuously perform processing of determining the connection state between the light guide 60 and the insertion member 20.

Therefore, the control unit 44 causes the test light source 12 to emit light at the frequency fb even after increasing the light emission amount of the illumination light source 11. That is, the test light source 12 is caused to emit light in the first pattern in which the on and off states of the pulse change at the frequency fb. After increasing the light emission amount of the illumination light source 11, the control unit 44 performs control to decrease the light amount of the illumination light source 11 in a case where it is determined that the light guide 60 and the insertion member 20 are not connected. For example, the control unit 44 adjusts the light emission amount of the illumination light source 11 to the same light amount in the connection determination period. After reducing the light amount of the illumination light source 11, the control unit 44 may continuously perform the connection state determination processing.

The illumination light generated from the illumination light source 11 after the connection is detected is illustrated on the right side of FIG. 5(A). The light emission frequency fa is the same as that before the connection is detected, but the light amount is increased as compared with that before the connection is detected. On the right side of FIG. 5(B), the test light generated from the test light source 12 after the connection is detected is illustrated. The frequency fb is the same as before the connection is detected, and the light amount is the same as before the connection is detected.

The right side of FIG. 5(C) illustrates light (superimposed light) generated from the light source device 10 (Illumination light source 11, test light source 12) and supplied to one end 61 of the light guide 60 after the connection is detected. The illumination light of the illumination light source 11 and the test light of the test light source 12 are superimposed in a cycle corresponding to the frequency fa, and only the test light of the test light source 12 is caused to emit light at the frequency fb in the other periods. Since the light amount of the illumination light is increased after the connection is detected, the light amount of the superimposed light of the illumination light and the test light is also larger than that before the connection is detected.

The display device 50 may display information indicating a detection result of the connection state performed by the control device 40. For example, when the control device 40 determines that the light guide 60 is not connected to the insertion member 20, the display device 50 may display a message (warning message) indicating that the light guide 60 is not connected. The display color of the warning message or the screen may be changed to a color indicating the warning. When the control device 40 determines that the light guide 60 is connected to the insertion member 20, the display device 50 may display a message (normal message) indicating that the light guide 60 is connected. The warning message or the normal message may be output by voice. The display device 50 may include a speaker that outputs sound. The control device 40 may transmit a warning message or a normal message to a terminal held by the user by wireless communication or wired communication. The control device 40 may include a communication unit that communicates with the terminal. The display device 50 and the speaker correspond to an example of an output unit that outputs information indicating a connection state between the light guide 60 and the insertion member 20.

As described above, according to the first embodiment, the illumination light blinking at the frequency fa and the test light blinking at the frequency fb are generated from the light source device 10, and the connection state between the light guide 60 and the insertion member 20 is determined on the basis of the image signal of the reflected light from the observation target S received by the camera head 30. By increasing the amount of illumination light only when it is determined that the light guide 60 and the insertion member 20 are connected, it is possible to prevent light exceeding an allowable amount from leaking from the other end 62 of the light guide 60.

First Modification

Figure 6:
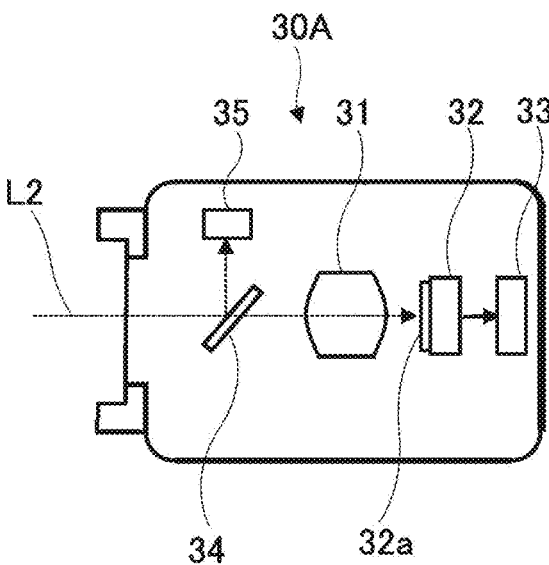
FIG. 6 is a diagram illustrating a configuration of a camera head in an endoscope device according to a modification of the first embodiment.

FIG. 6 illustrates a configuration example of a camera head 30A in an endoscope device 100 according to a first modification of the first embodiment. In addition to the lens unit 31, the imaging unit 32, and the communication unit 33, a half mirror 34 and a light amount detection sensor 35 are provided. The half mirror 34 reflects a part of the reflected light L2 incident on the imaging unit 32 to the light amount detection sensor 35. The half mirror 34 transmits the remaining part of the reflected light L2 and causes the reflected light L2 to be incident on the imaging unit 32 via the lens unit 31. The half mirror 34 functions as a first light splitting unit that splits the input reflected light L2 into the first split light and the second split light, reflects the first split light to the light amount detection sensor 35, and transmits the second split light. The light amount detection sensor 35 corresponds to a first light receiving sensor that receives a part (first split light) of the reflected light L2 reflected by the half mirror 34. The light amount detection sensor 35 operates at a detection rate (for example, a rate of twice or more the frequency fb) corresponding to the frequency fb of the test light, and detects the light amount of the incident light at the detection rate. The light amount detection sensor 35 transmits light amount information indicating the detected light amount to the control unit 44 via the communication unit 33. The light amount detection sensor 35 is, for example, a photoelectric sensor that converts detected light into an electric signal, and can be configured using a photodiode, a transistor, and the like.

The control unit 44 determines whether or not the other end 62 of the light guide 60 is connected to the insertion member 20 based on the light quantity information. The determination method is the same as that of the first embodiment. For example, in the connection determination period, the light quantity information is compared between the test light threshold value (lower limit A_1 and upper limit A_2) and the superimposed light threshold value (lower limit B_1 and upper limit B_2). A sequence of detection results is generated on the basis of comparison with these threshold values. The control unit 44 determines whether the unit sequence is included in the generated sequence of the detection result a predetermined number of times or more. In a case where the unit sequence is included in the sequence of the detection result a predetermined number of times or more, the control unit 44 detects that reflected light of light changing in the connection determination pattern is received. That is, the control unit 44 determines that the other end 62 of the light guide 60 is connected to the insertion member 20.

According to the first modification, it is not necessary for the imaging unit 32 to image an image of the test light emitted at the frequency fb, so that the frame rate of the imaging unit 32 can be set to a rate corresponding to the frequency fa of the illumination light. That is, the frame rate of the imaging unit 32 can be reduced. Therefore, the configuration of the imaging unit 32 can be simplified.

Second Modification

In the first embodiment, the pattern obtained by combining the emission pattern of the illumination light and the emission pattern of the test light is used as the connection determination pattern, but the emission pattern of the test light may be used as the connection determination pattern.

In this case, as a method of detecting whether the reflected light of the light changing in the connection determination pattern is received, luminance information of an image signal for each frame is measured, and the luminance information is compared with a threshold value (lower limit A_1 and upper limit A_2) for detecting the reflected light of the test light. As an example, during at least a part of the connection determination period, it is determined whether the luminance information of the lower limit A_1 or more and the upper limit A_2 or less and the luminance information of less than the lower limit A_1 are alternately detected a certain number of times or more for each frame. In a case where these pieces of luminance information are alternately detected a certain number of times or more, the control unit 44 detects that reflected light of light changing in the connection determination pattern is received.

Specifically, for example, the control unit 44 generates a detection result obtained by comparing the luminance information with a threshold value for each frame, and generates a sequence of detection results by arranging the detection results in time series. It is determined whether the sequence of the detection result includes a unit sequence (minimum unit of repetition of the detection result to be obtained with respect to the emission pattern of the test light) a predetermined number of times or more. In this example, since the connection determination pattern is a pattern in which the on/off pulse of the test light is repeated, a sequence (sequence A, X) in which the detection result (detection result A) equal to or more than the lower limit and equal to or less than the upper limit and the detection result (detection result X) less than the lower limit are arranged can be set as the unit sequence. When the unit sequence is included a predetermined number of times or more, it is detected that the reflected light of the test light is received.

In the period in which the test light and the illumination light are superimposed, the light amounts of the test light and the illumination light are summed. However, when the luminance information is larger than the upper limit, it can be considered that the test light is received, or it can be considered that the test light is not received. Even if it is assumed that the test light is not received, it is possible to detect the reception of the test light by decreasing the predetermined number of times (for example, once). According to the second modification, by using the emission pattern of the test light as the connection determination pattern, the connection determination process can be simplified.

Third Modification

In the first embodiment, the illumination light source 11 is caused to emit the illumination light before the connection between the light guide and the insertion member is detected. However, the control unit 44 may not emit the illumination light before the connection is detected, and may start emitting the illumination light after the connection is detected. In this case, it may take time until the image of the observation target S is visually recognized according to the time required to start the driving of the illumination light source 11 after the connection is detected, but there is an advantage that the power consumption before the connection is detected can be reduced.

Fourth Modification

In the first embodiment, the luminance information of the image signal obtained by imaging the reflected light is compared with the threshold value, and the connection state of the light guide is determined based on the comparison result for each image signal. However, the connection state may be determined using a learned model by machine learning such as a neural network. For example, the control unit 44 assigns luminance information based on an image signal corresponding to each frame in at least a part of the connection determination period to each input node of the neural network. Alternatively, a plurality of pixel values (for example, luminance values) included in the image signal corresponding to each frame is allocated to each input node. The control unit 44 performs weight calculation of the neural network and outputs information indicating the probability that the light guide is connected from the output node. The control unit 44 determines that the light guide is connected when the probability is a certain value or more, and determines that the light guide is not connected when the probability is less than the certain value. The output of the neural network is not limited to the probability, and may be, for example, information indicating whether or not the light guide is connected. In this case, the control unit 44 determines that the light guide is connected when the information indicates the presence of connection, and determines that the light guide is not connected when the information indicates the absence of connection. By determining the connection state using a machine learning model such as a neural network in this manner, it is possible to determine the presence or absence of connection of the light guide with high accuracy or easily even when the timings of light emission from the plurality of light sources are not synchronized. The machine learning model is not limited to the neural network, and other types of regression models such as a decision tree or a multiple regression model may be used.

Second Embodiment

Figure 7:
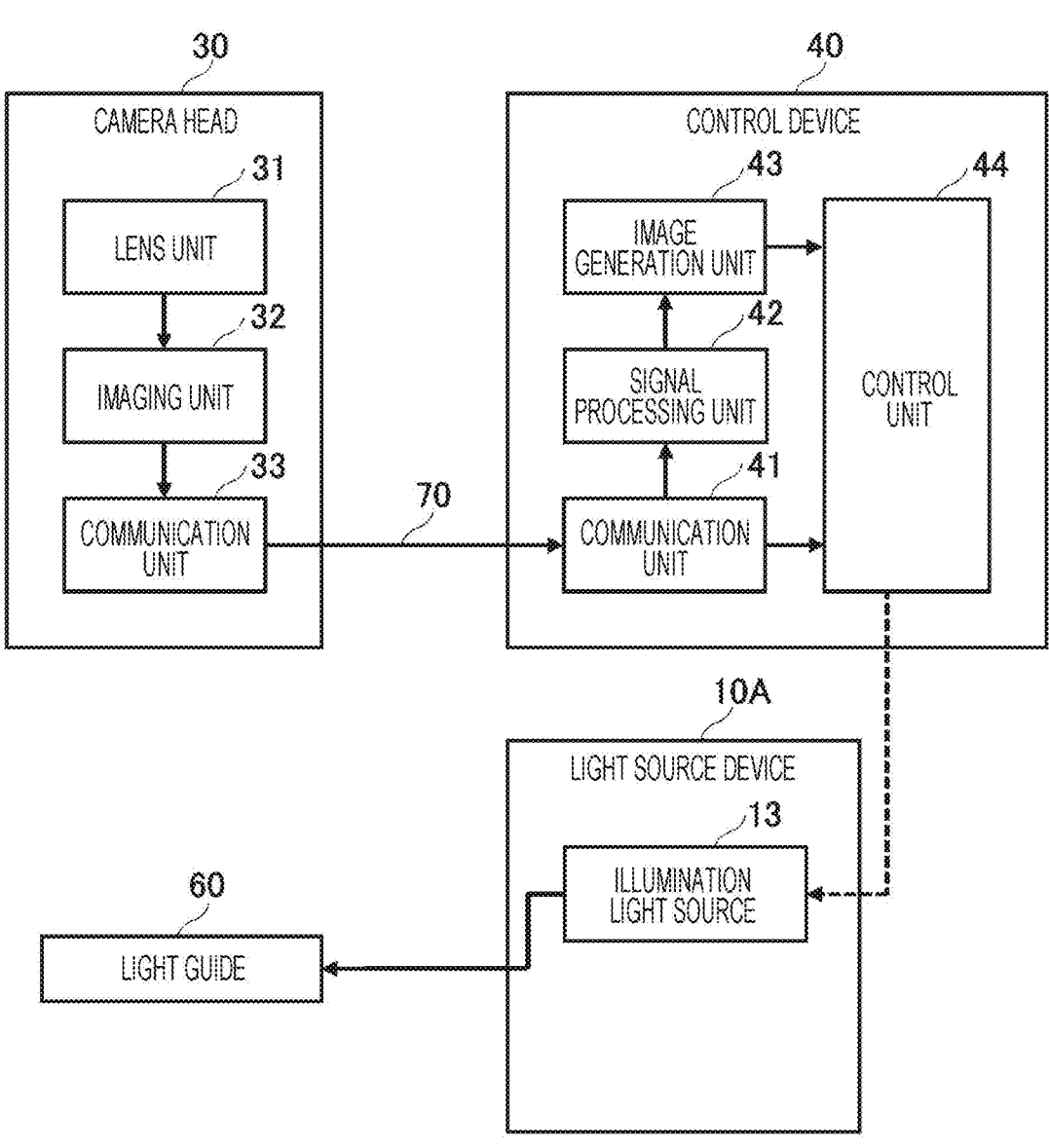
FIG. 7 is a detailed block diagram of a light source device, a camera head, and a control device included in an endoscope device according to a second embodiment.

In the first embodiment, the illumination light source 11 that generates the illumination light blinking at the frequency fa and the test light source 12 that generates the test light blinking at the frequency fb are used. On the other hand, in the second embodiment, the illumination light source 13 that generates the illumination light blinking at the frequency fc is used, and the illumination light also serves as the test light. FIG. 7 is a detailed block diagram of a light source device, a camera head, and a control device included in an endoscope device according to a second embodiment. The light source device 10A includes an illumination light source 13. The illumination light source 13 blinks at a frequency fc. When there is ambient light that blinks periodically like a fluorescent lamp, the frequency fc is preferably a value that can be distinguished from the frequency of the ambient light (for example, a frequency higher or lower than the frequency of the ambient light). The frequency fc is, for example, 300 Hz. However, the frequency of the illumination light is not limited to 300 Hz, and may be any frequency. The wavelength of the illumination light is not limited to a specific value or range. As an example, the illumination light may be visible light, infrared light, ultraviolet light, or the like. The illumination light may be laser light or the like. Hereinafter, differences from the first embodiment will be mainly described.

The light source device 10 generates illumination light blinking (pulsed lighting) at the frequency fc using the illumination light source 13.

Figure 8:
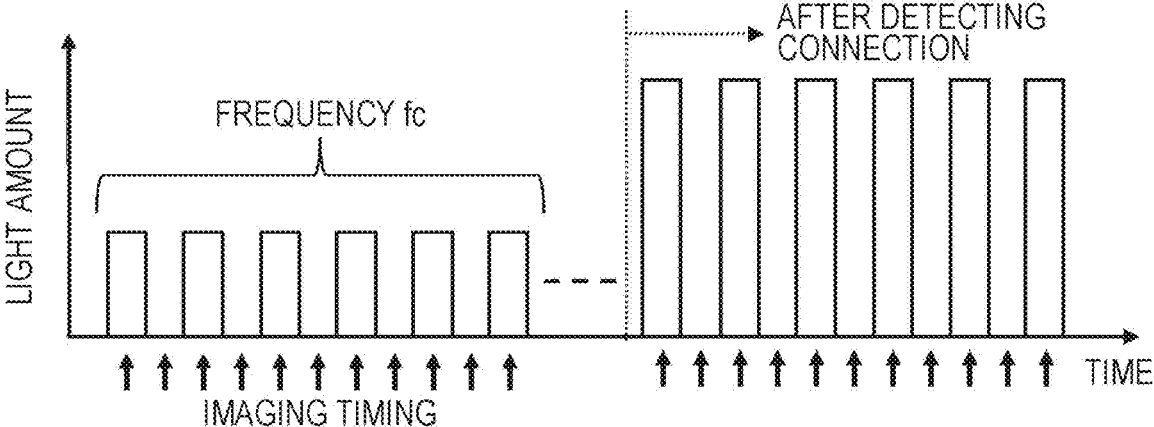
FIG. 8 is a view illustrating an example of illumination light according to the second embodiment.
Figure 9:
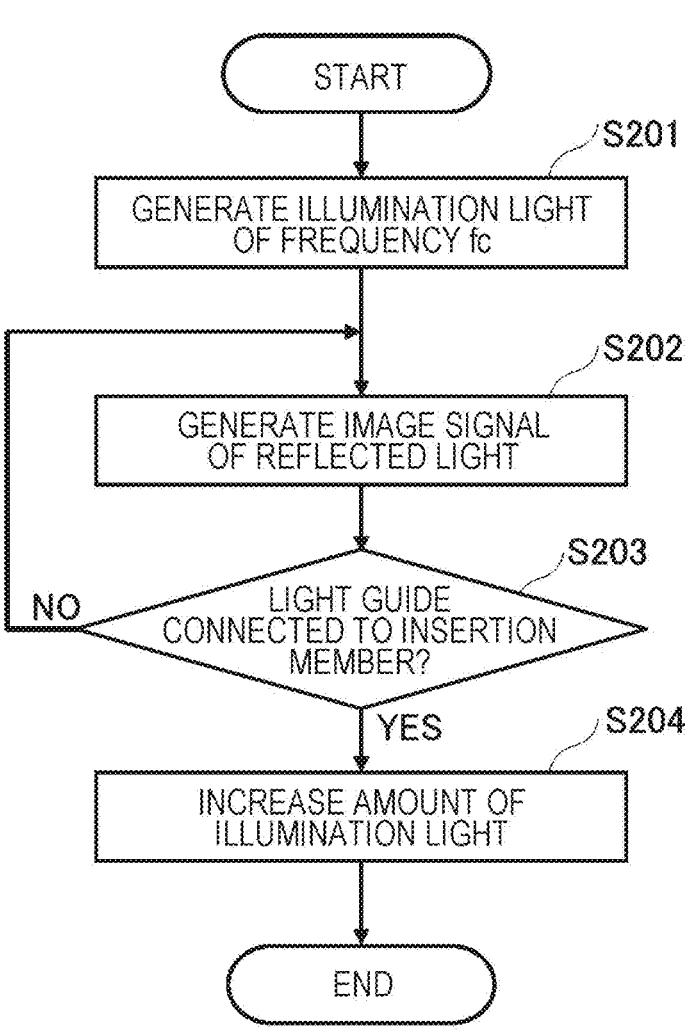
FIG. 9 is a flowchart illustrating determination processing of a connection state between a light guide and an insertion member in the endoscope device according to the second embodiment.

An example of the illumination light blinking (pulse lighting) at the frequency fc before the connection is detected is illustrated on the left side of FIG. 8. The frequency fc is, for example, 300 Hz. The generated illumination light is supplied to one end 61 of the light guide 60. Reflected light of the illumination light is imaged by the imaging element 32a of the camera head 30, and the imaging unit 32 generates an image signal at a frame rate corresponding to the frequency fc (for example, a frame rate of twice or more the frequency fc) as in the first embodiment. The control unit 44 of the control device 40 determines the connection state between the light guide 60 and the insertion member 20 on the basis of the image signal in the same manner as in the first embodiment. Hereinafter, details of this processing will be described with reference to FIG. 9. FIG. 9 is a flowchart of an example of determination processing of a connection state between the light guide 60 and the insertion member 20 according to the second embodiment.

In step S201, the control unit 44 of the control device 40 generates illumination light blinking at the frequency fc (for example, 300 Hz) from the illumination light source 13 of the light source device 10.

The light amount of the illumination light generated from the illumination light source 13 is suppressed to a light amount that ensures safety even if the light is emitted from the other end 62 of the light guide 60 in a state where the other end 62 of the light guide 60 is not connected to the insertion member 20.

In step S202, the imaging unit 32 of the camera head 30 images the reflected light from the observation target S at a frame rate (for example, 600 Hz) that is twice or more the frequency fc of the illumination light and converts the reflected light into an electric signal. Thus, for example, an image signal of 600 frames per second is generated. At this time, the imaging timing of the imaging unit 32 is synchronized with the blinking timing of the illumination light (see FIG. 8).

In step S203, the control unit 44 of the control device 40 determines whether or not the other end 62 of the light guide 60 is connected to the insertion member 20 based on the image signal for each frame generated by the imaging unit 32. The determination method may be the same as that of the first embodiment. For example, the luminance information of the image signal is compared with a threshold value (lower limit, upper limit) at which the reflected light of the illumination light can be detected. When the luminance information of the lower limit or more and the upper limit or less and the luminance information of the lower limit or less are alternately detected a certain number of times or more during at least a part of the connection determination period, it is detected that reflected light of light changing in the connection determination pattern is received. Specifically, for example, the control unit 44 generates a detection result obtained by comparing the luminance information with the lower limit and the upper limit for each frame, and generates a sequence of detection results by arranging the detection results in time series. It is determined whether the sequence of the detection result includes a unit sequence (minimum unit of repetition of the detection result to be obtained with respect to the emission pattern of the illumination light) determined according to the connection determination pattern a predetermined number of times or more. In this example, since the connection determination pattern is a pattern in which a pulse in which the illumination light is turned on and off is repeated, a sequence including two detection results of the lower limit or more and the upper limit or less and a detection result less than the lower limit can be set as the unit sequence.

In a case where it is determined in step S203 described above that the other end 62 of the light guide 60 is connected to the insertion member 20, in step S204, the control unit 44 increases the amount of illumination light generated from the illumination light source 13 of the light source device 10. For example, the amount of illumination light generated by the illumination light source 13 can be increased to the extent that the amount of light emitted from the emission unit 24A of the insertion member 20 falls within a safe range. The method of increasing the light amount may be the same as that in the first embodiment. Even after the light amount is increased, the determination processing of the connection state between the light guide 60 and the insertion member 20 may be continuously performed (see the right side of FIG. 8). In this case, as in the first embodiment, the threshold values (the lower limit and the upper limit) may be increased according to the increase in the light amount.

As described above, according to the second embodiment, the illumination light blinking at the frequency fc is generated from the light source device 10, and the connection state between the light guide 60 and the insertion member 20 is determined on the basis of the image signal of the reflected light from the observation target S detected by the camera head 30. For example, the control device 40 determines that the light guide 60 and the insertion member 20 are connected when an image signal having luminance corresponding to reflected light of the illumination light can be detected at a frequency corresponding to the frequency fc. After it is determined that the light guide 60 and the insertion member 20 are connected, the amount of illumination light is increased. As a result, it is possible to reliably prevent light exceeding an allowable amount from leaking from the other end 62 of the light guide 60.

Modification

A first modification (see FIG. 6) similar to the first embodiment is also applicable to the second embodiment. That is, it is only required that a half mirror and a light amount detection sensor be provided inside the camera head 30, and the light amount of the reflected light be detected by the light amount detection sensor. As a result, it is only required that only the light amount detection sensor be operated at a detection rate (for example, a rate of twice or more the frequency fc) corresponding to the frequency fc of the illumination light, and the imaging unit 32 be operated at a frame rate corresponding to a frequency lower than the frequency fc (for example, the frequency fa in the first embodiment). Therefore, the configuration of the imaging unit 32 can be simplified.

The fourth modification of the first embodiment is also applicable similarly to the second embodiment.

Third Embodiment

In the first embodiment described above, the illumination light generated from the illumination light source 11 of the light source device 10 is pulsed. On the other hand, in the third embodiment, the illumination light generated by the light source device 10 is a continuous wave.

Outputting continuous wave illumination light is referred to as continuous lighting.

Figure 10:
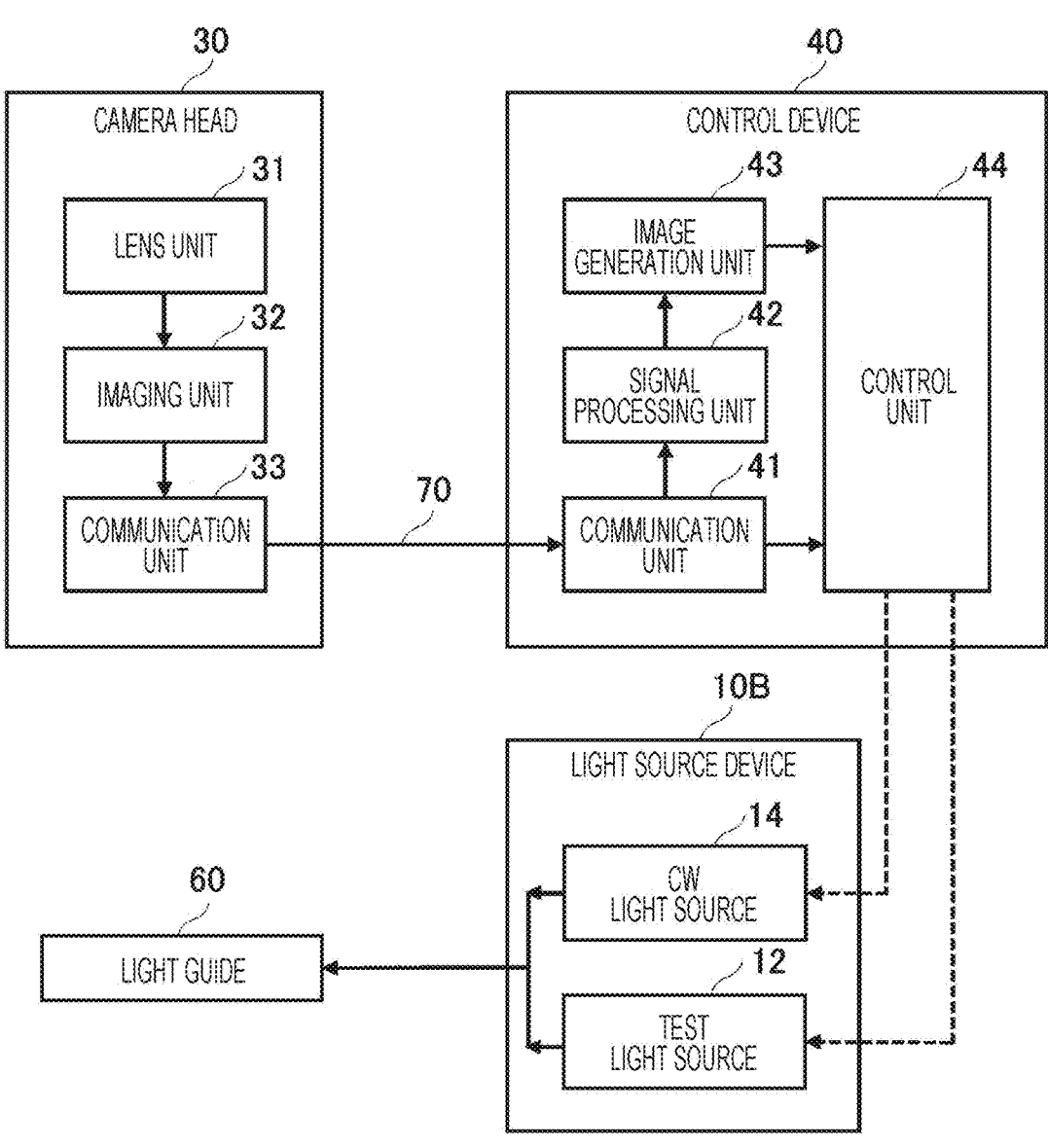
FIG. 10 is a detailed block diagram of a light source device, a camera head, and a control device included in an endoscope device according to a third embodiment.

FIG. 10 is a detailed block diagram of a light source device, a camera head, and a control device included in an endoscope device according to a third embodiment. The light source device 10B includes a test light source 12 that generates test light at a frequency fb, and a continuous wave (CW) light source 14 that generates a continuous wave (CW) as illumination light. The test light source 12 may be similar to the test light source 12 of the first embodiment. The wavelength of the illumination light generated from the CW light source 14 is not limited to a specific value or range. The illumination light may be, for example, visible light, infrared light, ultraviolet light, or the like. The illumination light may be laser light. The wavelength of the CW light source 14 and the wavelength of the test light source 12 may be the same or different.

The light source device 10B generates illumination light that is continuously lit using the CW light source 14, generates test light that blinks at the frequency fb using the test light source 12, and supplies light obtained by superimposing the illumination light and the test light to one end 61 of the light guide 60. The control device 40 or the control unit 44 in the control device 40 determines the connection state between the light guide 60 and the insertion member 20 based on the image signal of the reflected light detected by the camera head 30. Hereinafter, details of this processing will be described with reference to FIG. 11.

Figure 11:
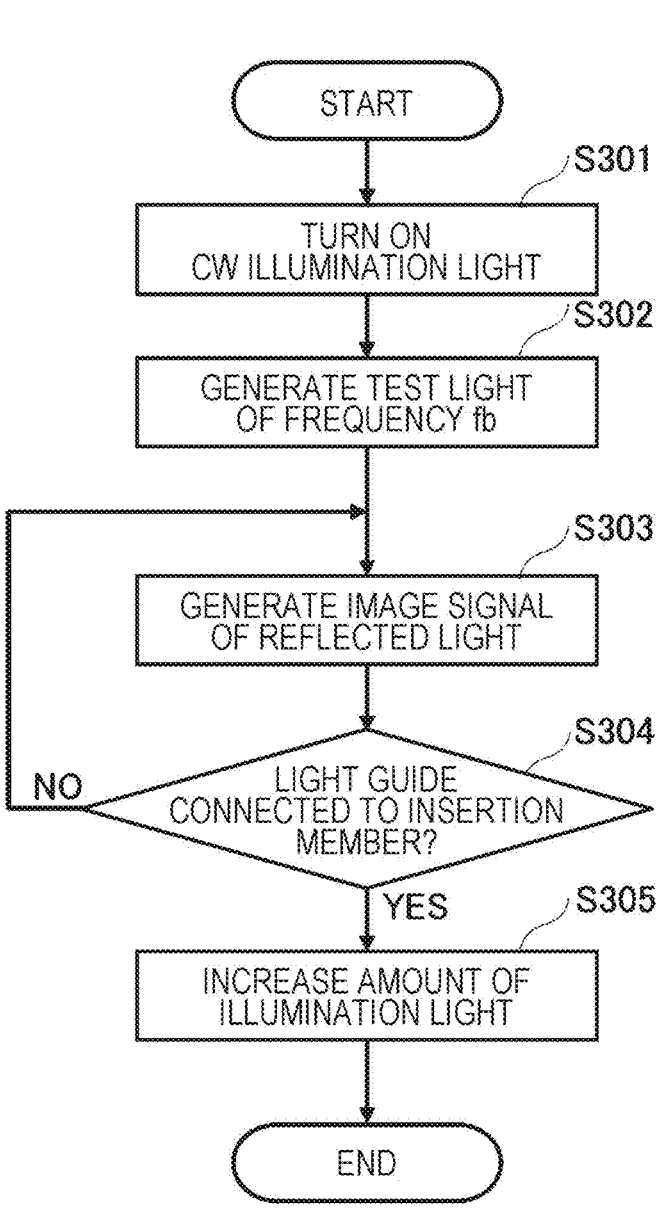
FIG. 11 is a flowchart illustrating determination processing of a connection state between a light guide and an insertion member in the endoscope device according to the third embodiment.

FIG. 11 is a flowchart of an example of determination processing of the connection state between the light guide 60 and the insertion member 20 according to the third embodiment.

In step S301, the control unit 44 of the control device 40 generates illumination light that is continuously turned on from the CW light source 14 of the light source device 10B.

Figure 12A:
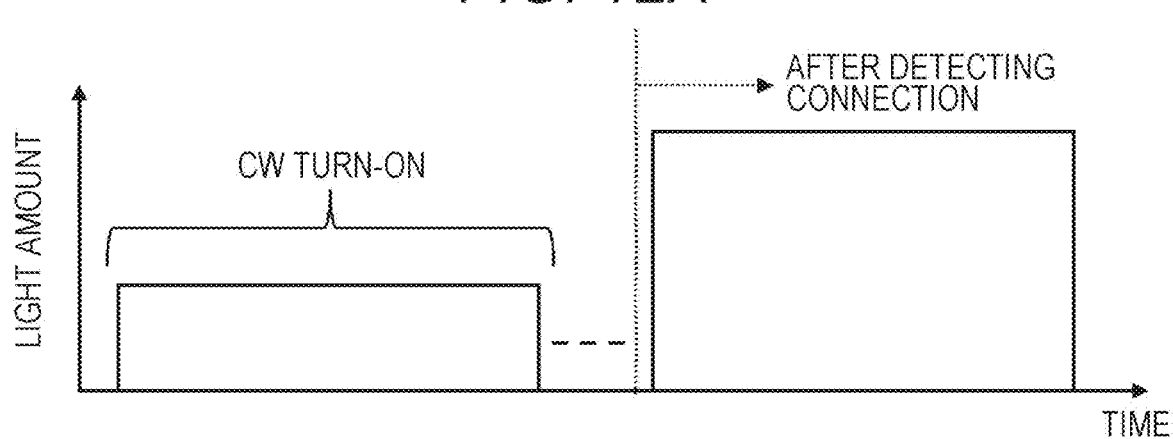
FIG. 12A is a view illustrating an example of illumination light, test light (FIG. 12B), and superimposed light thereof (FIG. 12C) according to the third embodiment.

An example of continuous light generated by the CW light source 14 before connection detection is illustrated on the left side of FIG. 12(A).

In step S302, the control unit 44 of the control device 40 generates test light blinking at the frequency fb (for example, 300 Hz) from the test light source 12 of the light source device 10B. Step S302 may be executed simultaneously with step S301.

Figure 12B:
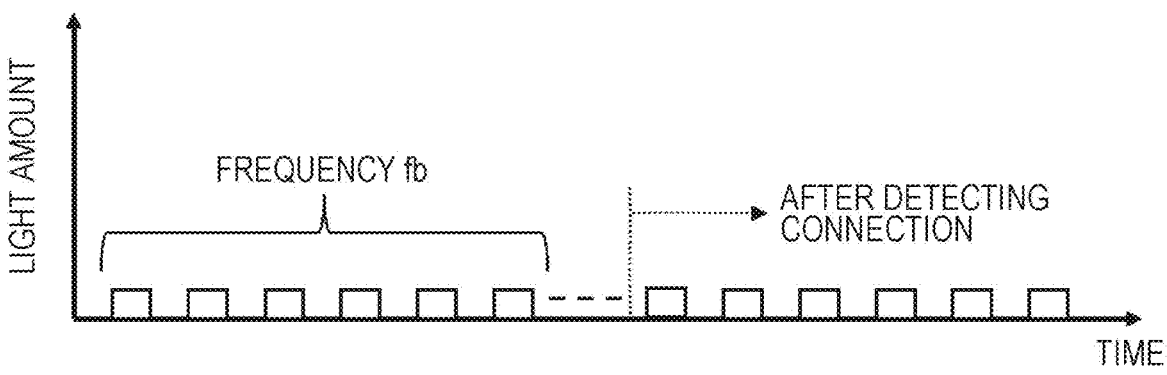

An example of the test light blinking (pulse lighting) at the frequency fb and generated by the test light source 12 before the connection is detected is illustrated on the left side of FIG. 12(B). In this example, the frequency fb is 300 Hz.

The light amount generated by the light source device 10 is suppressed to a light amount (allowable amount) that ensures safety even if light is emitted from the other end 62 of the light guide 60 in a state where the other end 62 of the light guide 60 is not connected to the insertion member 20 when the illumination light and the test light are simultaneously generated.

During a period in which the illumination light (continuous light) and the test light are simultaneously turned on, the illumination light and the test light are superimposed, and the superimposed light is supplied to one end 61 of the light guide 60. During a period other than the synchronous lighting period, only the continuous light is supplied to the one end 61 of the light guide 60.

Figure 12C:
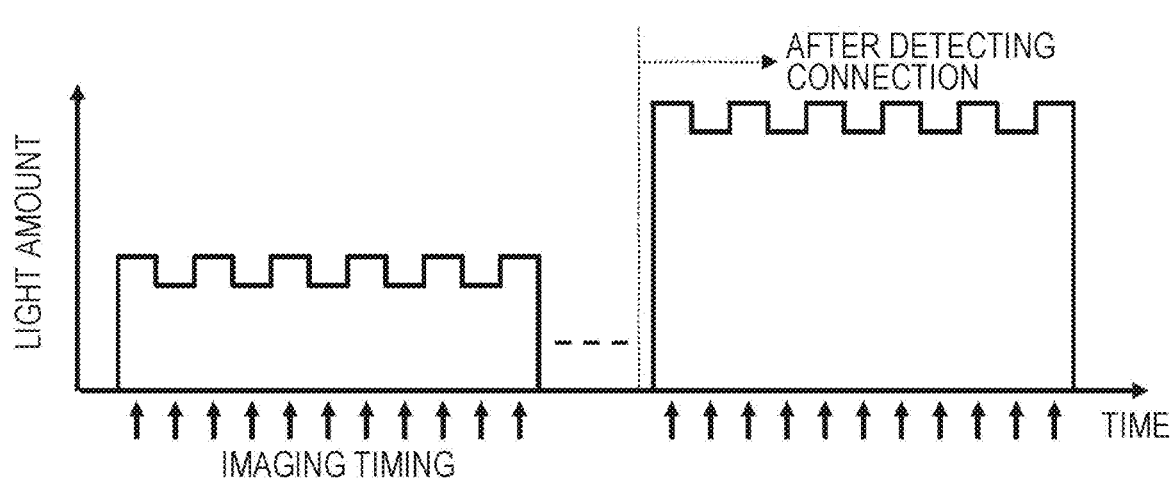

On the left side of FIG. 12(C), an example of light generated from the light source device 10B (CW light source 14, test light source 12) before detection of connection and supplied to one end 61 of the light guide 60 is illustrated. This light is obtained by adding the light on the left side of FIG. 12(A) and the light on the left side of FIG. 12(B) at the same time.

In step S303, the imaging unit 32 of the camera head 30 images the reflected light from the observation target S at a frame rate corresponding to the frequency fb of the test light (for example, a frame rate that is twice or more the frequency fb) and converts the reflected light into an electric signal. The reflected light from the observation target S is reflected light of light in which the illumination light and the test light are superimposed, or reflected light of continuous light. In a case where the frequency fb is 300 Hz, the imaging unit 32 performs imaging at a frame rate of 600 Hz that is twice the frame rate according to the frequency fb. As a result, an image signal of 600 frames per second is generated. At this time, the imaging timing of the imaging unit 32 is synchronized with the blinking timing of the test light (see FIG. 12(C)).

In step S304, the control unit 44 of the control device 40 determines whether or not the other end 62 of the light guide 60 is connected to the insertion member 20 based on the image signal for each frame generated by the imaging unit 32. The control unit 44 compares the luminance information of the image signal with the threshold value for each frame of the image signal. The threshold value is a threshold value (lower limit B_1 and upper limit B_2) with which the superimposed light of the illumination light (continuous wave) and the test light can be detected. For example, in a case where luminance information of a lower limit or more and an upper limit or less and luminance information of a value less than the lower limit are alternately detected a certain number of times in at least a part of the connection determination period, it is detected that reflected light of light changing in the connection determination pattern is received. In this case, the control unit 44 determines that the other end 62 of the light guide 60 is connected to the insertion member 20.

A method for determining the threshold value capable of detecting the superimposed light of the illumination light (continuous light) and the test light may be the same method as in the first embodiment. For example, the illumination light (continuous light) and the test light are emitted to image the reflected light of the superimposed light, and the maximum luminance or the minimum luminance of the image signal is calculated once or a plurality of times. An upper limit reference value such as a maximum value or an average value of the plurality of maximum luminance values, or a value obtained by adding a constant value (margin value) to the upper limit reference value is set as the upper limit. Similarly, a lower limit reference value such as a minimum value or an average value among the plurality of minimum luminance values, or a value obtained by subtracting a certain value (margin value) from the lower limit reference value is set as the lower limit.

Alternatively, the threshold value may be determined on the basis of knowledge of a user such as a physician. The threshold value is desirably larger than a threshold value at which only continuous light can be detected.

In a case where it is determined in step S304 described above that the other end 62 of the light guide 60 is connected to the insertion member 20, in step S305, the control unit 44 increases the light amount of the illumination light (continuous wave light) generated from the CW light source 14 of the light source device 10. The amount of illumination light generated by the CW light source 14 can be increased to the extent that the amount of light emitted from the emission unit 24A of the insertion member 20 falls within a safe range. The method of increasing the light amount may be the same as that in the first embodiment.

After increasing the light emission amount of the CW light source 14 (after detecting the connection), the control unit 44 may continuously perform a process of determining the connection state between the light guide 60 and the insertion member 20. Therefore, even after increasing the light emission amount of the CW light source 14, the control unit 44 causes the test light source 12 to emit light at the frequency fb. Since the light amount of the CW light source 14 increases after the connection is detected, the threshold values (the lower limit and the upper limit) for detecting the superimposed light of the illumination light and the test light may be changed to large values. The method for determining the changed threshold value may be similar to the method for determining the pre-change threshold value described above. When determining that the light guide 60 and the insertion member 20 are not connected, the control unit 44 decreases the light amount of the CW light source 14. For example, the light emission amount of the CW light source 14 is set to the same light amount as the light amount used in the connection determination period. After reducing the light amount of the CW light source 14, the control unit 44 may continuously perform the connection state determination processing.

On the right side of FIG. 12(A), continuous light (illumination light) generated from the CW light source 14 after the connection is detected is illustrated. The amount of continuous light is larger than that before connection detection.

The right side of FIG. 12(B) illustrates the test light generated from the test light source 12 after the connection is detected. The frequency fb is the same as before the connection is detected, and the light amount is the same as before the connection is detected.

The right side of FIG. 12(C) illustrates the light generated from the light source device 10B (CW light source 14, test light source 12) and supplied to one end 61 of the light guide 60 after the connection is detected. The illumination light of the CW light source 14 and the test light of the test light source 12 are superimposed in a cycle corresponding to the frequency fb. In the other periods, only the continuous wave light of the CW light source 14 is emitted.

As described above, according to the third embodiment, even in a case where the continuous light is used as the illumination light from the light source device 10, the connection state between the light guide 60 and the insertion member 20 can be determined.

Modification

A first modification (see FIG. 6) similar to the first embodiment is also applicable to the third embodiment. That is, it is only required that a half mirror and a light amount detection sensor be provided inside the camera head 30, and the light amount of the reflected light be detected by the light amount detection sensor. As a result, it is only required that the light amount detection sensor be operated at a detection rate (for example, a rate of twice or more the frequency fb) corresponding to the frequency fb of the test light, and the imaging unit 32 be operated at a frame rate of the frequency fa lower than the frequency fb. Thus, the configuration of the imaging unit 32 can be simplified. Second to fourth modifications similar to the first embodiment are also applicable to the second embodiment.

Fourth Embodiment

In the first to third embodiments described above, it is detected whether the reflected light of the test light emitted at the frequency fb or the like is received on the basis of the imaged image of the reflected light from the observation target S, and the connection state between the light guide 60 and the insertion member 20 is determined on the basis of the detection result. On the other hand, in the fourth embodiment, the connection state between the light guide 60 and the insertion member 20 is determined based on the wavelength included in the reflected light from the observation target S.

Figure 13:
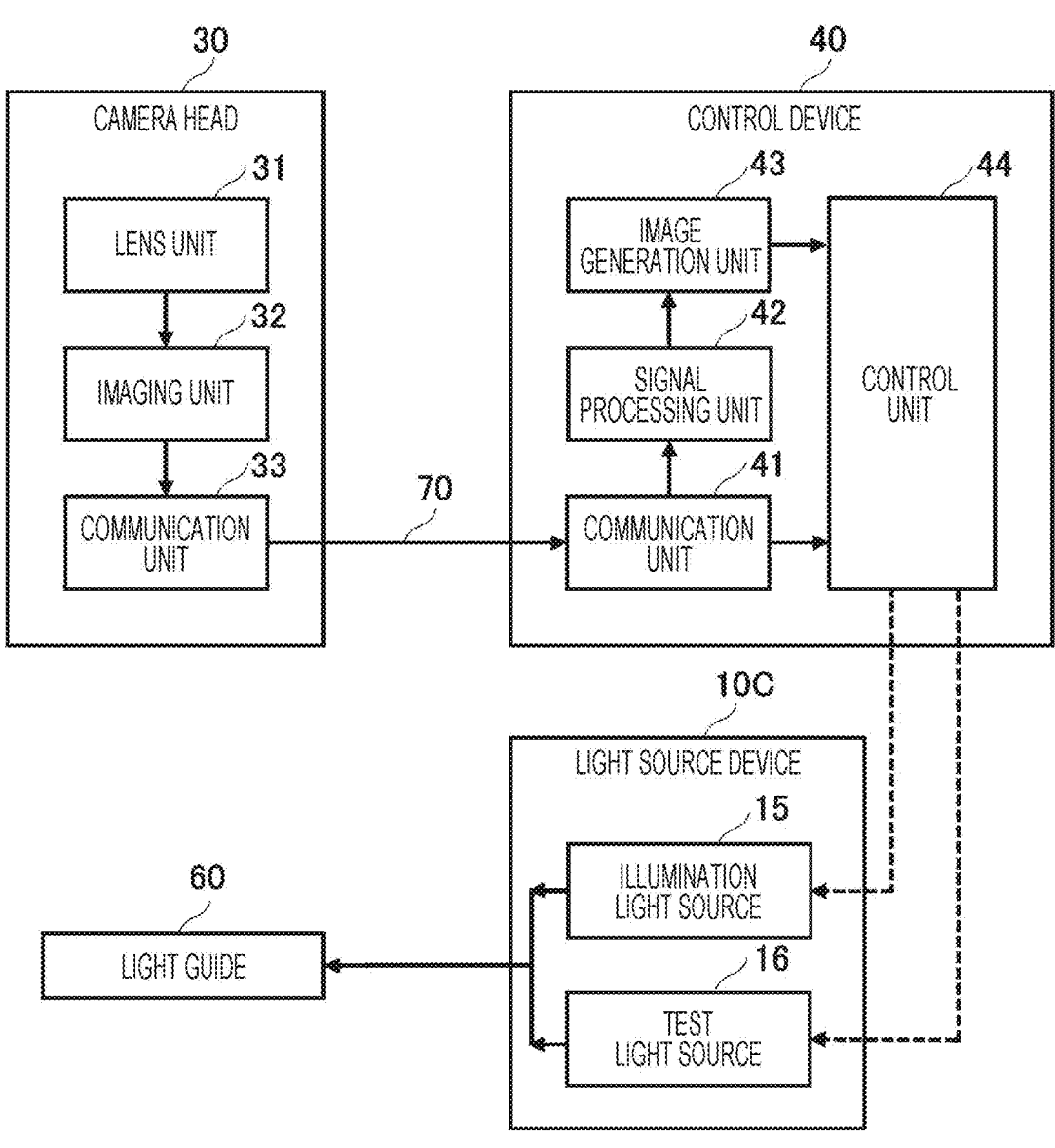
FIG. 13 is a detailed block diagram of a light source device, a camera head, and a control device included in an endoscope device according to a fourth embodiment.

FIG. 13 is a detailed block diagram of a light source device, a camera head, and a control device included in an endoscope device according to a fourth embodiment. The light source device 10C includes an illumination light source 15 that generates illumination light in a wavelength range Ra and a test light source 16 that generates a wavelength range Rb different from the wavelength range Ra. The light belonging to the wavelength range Rb corresponds to fourth light that is light including a first wavelength for connection state determination, and the light belonging to the wavelength range Ra corresponds to fifth light that is light including a second wavelength for living body observation.

The wavelength range Ra of the illumination light generated by the illumination light source 15 is not limited to a specific value or range. In the present example, the wavelength range Ra is a wavelength range of visible light (about 380 nm to 780 nm). The illumination light in the wavelength range Ra may be laser light.

The wavelength range Rb of the illumination light generated by the test light source 16 is not limited to a specific value or range. When the disturbance light is present, the wavelength range Rb is preferably different from the wavelength range of the disturbance light. In the present example, the wavelength range Rb is a wavelength range of ultraviolet rays (about 10 nm to 380 nm). The test light may be a laser beam.

The light source device 10C emits illumination light in the wavelength range Ra using the illumination light source 15, and generates test light in the wavelength range Rb using the test light source 16. The light emission timing of the test light can be determined independently of the illumination light. As an example, the light emission timing of the test light may be periodic or aperiodic. The light emission timing of the test light may or may not be the same as that of the illumination light. Similarly to the first embodiment, the frequency of the illumination light may be, for example, 60 Hz, and the frequency of the test light may be, for example, 300 Hz. In this example, it is assumed that the test light and the illumination light are simultaneously emitted at the same cycle. The light source device 10C supplies light in which the test light and the illumination light are superimposed to one end 61 of the light guide 60.

Figure 14:
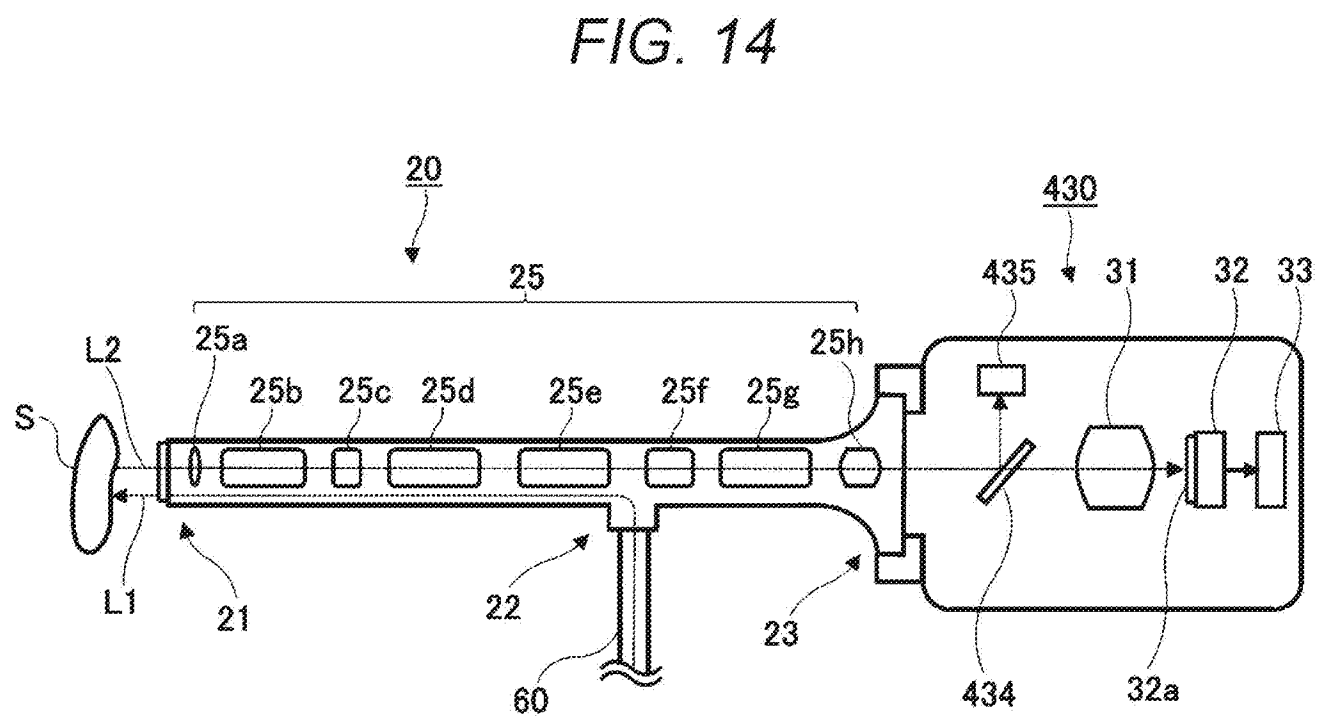

FIG. 14 is a diagram illustrating an internal configuration of the insertion member 20 and the camera head 430. The configuration of the insertion member 20 is similar to that of the first embodiment. The camera head 430 includes a dichroic mirror 434 that transmits the light in the wavelength range Ra and reflects the light in the wavelength range Rb among the reflected light, and a light receiving sensor 435 that receives the light reflected by the dichroic mirror 434. As an example, the light receiving sensor 435 includes a photoelectric sensor, a band-pass filter that passes a signal in the wavelength range Rb, and the like. The light receiving sensor 435 corresponds to a second light receiving sensor that receives light reflected by the dichroic mirror 434. The light receiving sensor 435 converts the received light into an electrical signal by the photoelectric sensor and inputs the electrical signal to the band-pass filter. The light receiving sensor 435 transmits amplitude information indicating the amplitude of the signal that has passed through the band-pass filter to the control unit 44. The amplitude information is an example of information included in light (reflected light) received by the light receiving sensor 435. The control unit 44 receives the amplitude information from the light receiving sensor 435 via the communication unit 41, and detects whether light in the wavelength range Rb (reflected wave of the test signal) is received by the light receiving sensor 435 on the basis of the amplitude information. That is, it is detected whether the reflected light includes light in the wavelength range Rb. When the value of the amplitude information is equal to or larger than the threshold value, it is detected that the light in the wavelength range Rb is received, that is, that the reflected light includes the light in the wavelength range Rb. Hereinafter, details of the processing will be described with reference to the flowchart of FIG. 15.

Figure 15:
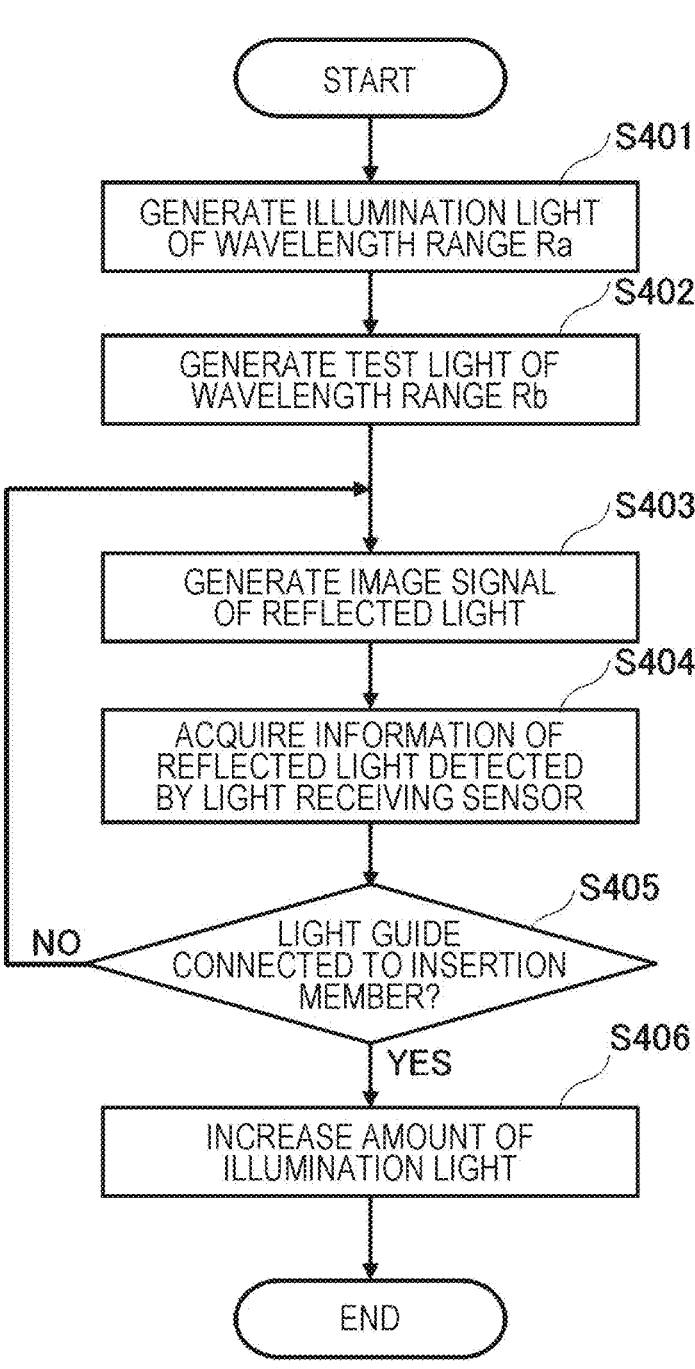
FIG. 15 is a flowchart for describing determination processing of a connection state between the light guide and the insertion member in the endoscope device according to the fourth embodiment.

FIG. 15 is a flowchart of an example of determination processing of the connection state between the light guide 60 and the insertion member 20 according to the fourth embodiment.

In step S401, the control unit 44 of the control device 40 generates the illumination light of the wavelength range Ra from the illumination light source 15 of the light source device 10C.

In step S402, the control unit 44 of the control device 40 generates test light of a wavelength range Rb different from the wavelength range Ra from the test light source 16 of the light source device 10C.

Figure 16:
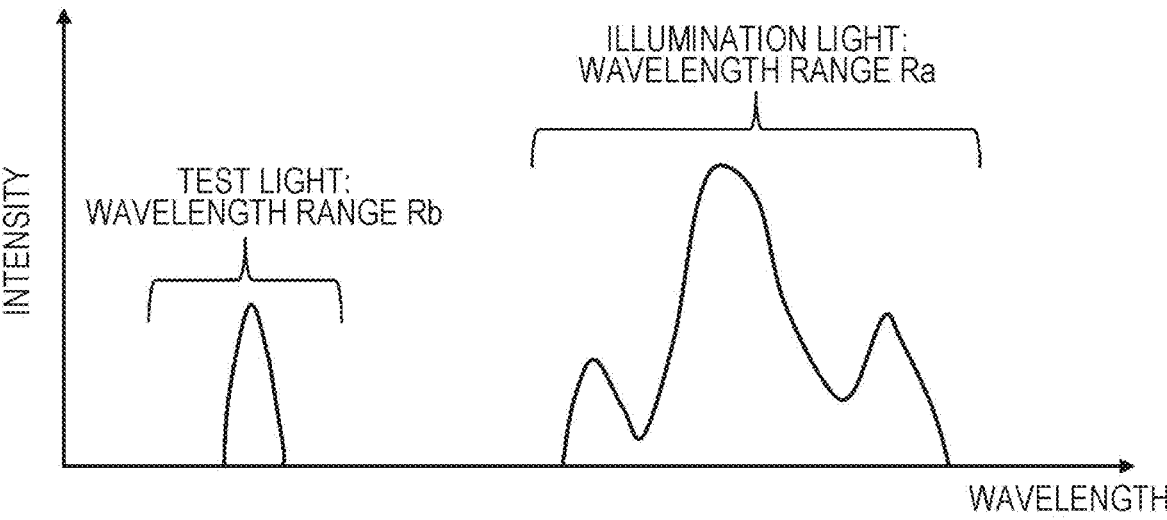
FIG. 16 is a view illustrating an example of illumination light and test light according to the fourth embodiment.

FIG. 16 illustrates an example of the illumination light in the wavelength range Ra generated from the illumination light source 15 and an example of the test light in the wavelength range Rb generated from the test light source 16. The horizontal axis represents wavelength, and the vertical axis represents intensity. In this example, the illumination light is assumed to be visible light. When the illumination light is excitation light of fluorescence, the illumination light is distributed on a wavelength side higher than visible light.

The light amount generated by the light source device 10, that is, the total light amount of the illumination light and the test light (for example, the light amount per unit time) is suppressed to a light amount that ensures safety even if the light is emitted from the other end 62 of the light guide 60 in a state where the other end 62 is not connected to the insertion member 20.

The illumination light in the wavelength range Ra and the test light in the wavelength range Rb are supplied to one end 61 of the light guide 60. The light supplied to the one end 61 propagates to the other end 62 of the light guide 60 and is emitted to the observation target S via the insertion member 20, and the reflected light from the observation target S is incident on the camera head 430. Of the reflected light incident on the camera head 430, the light in the wavelength range Rb is reflected by the dichroic mirror 434 to the light receiving sensor 435. Of the reflected light incident on the camera head 430, light in the wavelength range Ra passes through the dichroic mirror 434 and forms an image on the imaging element 32a of the imaging unit 32.

In step S403, the imaging unit 32 of the camera head 30 images the light in the wavelength range Ra formed on the imaging element 32a at a predetermined frame rate, and generates an image signal for each frame. As an example, in a case where the illumination light is pulsed light emission, the predetermined frame rate may be the same as the frequency of the pulse.

In step S404, the control unit 44 of the control device 40 acquires information of the reflected light detected by the light receiving sensor 435 of the camera head 30 from the camera head 30. For example, the control unit 44 acquires amplitude information regarding the reflected light detected by the light receiving sensor 435 from the camera head 30.

In step S405, the control unit 44 determines whether or not the other end 62 of the light guide 60 is connected to the insertion member 20 on the basis of the amplitude information (information of the reflected light) acquired from the light receiving sensor 435. Specifically, the control unit 44 detects whether or not the light detected by the light receiving sensor 435 includes light in the wavelength range Rb on the basis of amplitude information (information of reflected light). When the amplitude information is equal to or larger than the threshold value, it is detected that the light detected by the light receiving sensor 435 includes the light in the wavelength range Rb. When the light detected by the light receiving sensor 435 includes the light in the wavelength range Rb, the control unit 44 determines that the other end 62 of the light guide 60 is connected to the insertion member 20. That is, when the other end 62 of the light guide 60 is connected to the insertion member 20, the reflected light from the observation target S includes the light in the wavelength range of the test light, that is, the wavelength range Rb. The light in the wavelength range Rb is reflected by the dichroic mirror 434 to the light receiving sensor 435. Therefore, it is possible to determine that the other end 62 of the light guide 60 is connected to the insertion member 20 by detecting that the light in the wavelength range Rb is included from the reflected light detected by the light receiving sensor 435.

On the other hand, when the amplitude information is less than the threshold value, the control unit 44 detects that the light detected by the light receiving sensor 435 does not include the light in the wavelength range Rb. When the light in the wavelength range Rb is not included in the reflected light detected by the light receiving sensor 435, it is determined that the other end 62 of the light guide 60 is not connected to the insertion member 20. That is, when the other end 62 of the light guide 60 is not connected to the insertion member 20, the reflected light from the observation target S does not include the light in the wavelength range of the test light, that is, the wavelength range Rb. Therefore, when the wavelength range Rb is not detected from the information of the reflected light received by the light receiving sensor 435, it can be determined that the other end 62 of the light guide 60 is not connected to the insertion member 20.

In a case where it is determined in step S405 described above that the other end 62 of the light guide 60 is connected to the insertion member 20, in step S406, the control unit 44 increases the amount of illumination light generated by the illumination light source 15 of the light source device 10. The amount of illumination light generated by the illumination light source 15 can be increased to the extent that the amount of light emitted from the emission unit 24A of the insertion member 20 falls within a safe range (allowable amount). The method of increasing the light amount may be the same as that in the first embodiment.

The control unit 44 may continuously perform a process of determining the connection state between the light guide 60 and the insertion member 20 even after increasing the light emission amount of the illumination light source 15 (after detecting the connection). Therefore, even after increasing the light emission amount of the illumination light source 15, the control unit 44 causes the test light source 16 to emit light in the same manner as before the connection is detected. When determining that the light guide 60 and the insertion member 20 are not connected, the control unit 44 decreases the light amount of the illumination light source 15. For example, the control unit 44 sets the light emission amount of the illumination light source 15 to the same light amount before the connection is detected. After reducing the light amount of the illumination light source 15, the control unit 44 may continuously perform the connection state determination processing.

As described above, according to the fourth embodiment, the connection state between the light guide 60 and the insertion member 20 can be determined even when the test light having the wavelength different from that of the illumination light is used.

Although some embodiments of the present disclosure have been described, these embodiments have been presented as examples and are not intended to limit the scope of the disclosure, and these embodiments can be implemented in various other embodiments and various omissions, substitutions, and changes can be made without departing from the gist of the disclosure. These embodiments and modifications thereof are included in the scope and gist of the disclosure and are included in the disclosure described in the claims and the equivalent scope thereof. Furthermore, the effects of the present disclosure described in the present specification are merely examples, and other effects may be provided. Note that the present disclosure can also have the following configurations.

Item 1

An endoscope device including:

a light source unit configured to supply light to one end of a light guide;

an insertion member including a connecting portion detachably connected to the other end of the light guide and a distal end that emits the light from the light guide to a target region of a subject;

a light receiving unit configured to receive reflected light reflected by the target region of the subject and incident from the distal end; and a control unit configured to determine a connection state between the light guide and the insertion member on the basis of information of the reflected light received by the light receiving unit.

Item 2

The endoscope device according to item 1, in which the light source unit supplies first light that is light changing in a first emission pattern with time, and the control unit detects whether reflected light of the first light is received on the basis of the information of the reflected light, and determines that the light guide is connected to the insertion member when the reflected light of the first light is received.

Item 3

The endoscope device according to item 2, in which the first emission pattern is a pattern in which light emission and non-light emission are repeated at a first time interval.

Item 4

The endoscope device according to item 2 or 3, in which the light receiving unit includes an imaging unit that images the reflected light and generates an image signal, and the control unit detects whether reflected light of the first light is received on the basis of the image signal.

Item 5

The endoscope device according to any one of items 1 to 4, in which the control unit increases a light amount of the light supplied from the light source unit when determining that the light guide is connected to the insertion member.

Item 6

The endoscope device according to any one of items 2 to 4, in which the light source unit supplies, to the one end of the light guide, second light that is light that is at least partially superimposed on the first light and changes in a second emission pattern with time, and the control unit detects whether reflected light of third light changing in a combined pattern obtained by combining the first emission pattern and the second emission pattern is received on the basis of the information of the reflected light, and determines that the light guide is connected to the insertion member when the reflected light of the third light is received.

Item 7

The endoscope device according to item 6, in which the light receiving unit includes an imaging unit that images the reflected light and generates an image signal, and the light receiving unit detects whether the reflected light of the third light is received on the basis of the image signal.

Item 8

The endoscope device according to item 7, in which the control unit increases a light amount of the second light supplied from the light source unit when determining that the light guide is connected to the insertion member.

Item 9

The endoscope device according to any one of items 6 to 8, in which the first emission pattern is a pattern in which light emission and non-light emission are repeated at a first time interval, and the second emission pattern is a pattern in which light emission and non-light emission are repeated at a second time interval longer than the first time interval.

Item 10

The endoscope device according to item 9, in which a light amount of the first light is smaller than a light amount of the second light.

Item 11

The endoscope device according to any one of items 6 to 9, in which the second light is continuous light.

Item 12

The endoscope device according to any one of items 6 to 11, further including:

a first light splitting unit configured to split the reflected light into first split light and second split light, in which the light receiving unit includes an imaging unit that images the second split light and generates an image signal for display, and a first light receiving sensor that receives the first split light, and the control unit detects whether the reflected light of the third light is received by the light receiving unit on the basis of information of the first split light received by the first light receiving sensor.

Item 13

The endoscope device according to item 12, in which the first light splitting unit is a half mirror that reflects the first split light to the first light receiving sensor and transmits the second split light to the imaging unit.

Item 14

The endoscope device according to any one of items 1 to 13, in which the light supplied from the light source unit includes a first wavelength, and the control unit determines whether the first wavelength is included in the reflected light on the basis of the information of the reflected light, and determines that the light guide is connected to the insertion member when the first wavelength is included.

Item 15

The endoscope device according to item 14, in which the light supplied from the light source unit includes the first wavelength and a second wavelength,

the light receiving unit includes:
a second light splitting unit configured to split the reflected light into fourth light including the first wavelength and fifth light including the second wavelength; and
a second light receiving sensor configured to receive the fourth light,
the light receiving unit includes an imaging unit that images the fifth light and generates an image signal for display, and
the control unit detects whether the first wavelength is included in the reflected light on the basis of information of the fourth light.

Item 16

The endoscope device according to item 15, in which
the second light splitting unit is a dichroic mirror that reflects the fourth light to the second light receiving sensor and transmits the fifth light to the imaging unit.

Item 17

The endoscope device according to any one of items 14 to 16, in which
the first wavelength is included in a wavelength range of ultraviolet rays.

Item 18

The endoscope device according to any one of items 1 to 17, further including:
an output unit configured to output information indicating a connection state between the light guide and the insertion member on the basis of a determination result of the control unit.

Item 19

The endoscope device according to any one of items 2 to 4, in which
a frequency of the first light is different from a frequency of disturbance light that can be mixed into the insertion member.

Item 20

The endoscope device according to any one of items 1 to 19, further including the light guide.

Item 21

A connection determination method including:
supplying light from a light source unit to one end of a light guide;
guiding light emitted by the light source unit to an insertion member to which the other end of the light guide is detachable;
emitting the light from a distal end of the insertion member to a target region of a subject;
receiving reflected light reflected by the target region and incident from the distal end of the insertion member; and
determining a connection state between the light guide and the insertion member on the basis of information of the received reflected light.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

10 Light source device
11 Illumination light source
12 Test light source
13 Illumination light source
14 CW light source
15 Illumination light source
16 Test light source
20 Insertion member (endoscope main body)
21 Distal end
22 Connecting portion
23 Base end
24A Emission unit
24B Incident portion
25 Observation optical system
30 Camera head (light receiving unit)
31 Lens unit
32 Imaging unit (light receiving unit)
32a Imaging element
33 Communication unit
34 Half mirror (first light splitting unit)
35 Light amount detection sensor (first light receiving sensor)
40 Control device
41 Communication unit
42 Signal processing unit
43 Image generation unit
44 Control unit
50 Display device (display unit, output unit)
60 Light guide
61 One end
62 Other end
70 Transmission cable
100 Endoscope device
430 Camera head (light receiving unit)
434 Dichroic mirror (second light splitting unit)
435 Light receiving sensor (second light receiving sensor)

The invention claimed is:
1. An endoscope device comprising:
a light source configured to supply first light that is changing in a first emission pattern with time and a second light that is at least partially superimposed on the first light and changes in a second emission pattern with time to one end of a light guide;
an insertion member including a connecting portion detachably connected to the other end of the light guide and a distal end that emits the light from the light guide to a target region of a subject;
a camera head configured to receive reflected light reflected by the target region of the subject and incident from the distal end; and
a control circuit configured to
detect whether reflected light of third light changing in a combined pattern obtained by combining the first emission pattern and the second emission pattern is received on a basis of the information of the reflected light, and
determine that the light guide is connected to the insertion member when the reflected light of the third light is received.

2. The endoscope device according to claim 1, wherein the first emission pattern is a pattern in which light emission and non-light emission are repeated at a first time interval.

3. The endoscope device according to claim 1, wherein the camera head includes a camera that images the reflected light and generates an image signal, and the control circuit is configured to detect whether reflected light of the first light is received on a basis of the image signal.

4. The endoscope device according to claim 1, wherein the control circuit is configured to increase a light amount of the light supplied from the light source when determining that the light guide is connected to the insertion member.

5. The endoscope device according to claim 1, wherein the camera head includes an image sensor that images the reflected light and generates an image signal, and the camera head detects whether the reflected light of the third light is received based on the image signal.

6. The endoscope device according to claim 5, wherein the control circuit is configured to increase a light amount of the second light supplied from the light source when determining that the light guide is connected to the insertion member.

7. The endoscope device according to claim 1, wherein the first emission pattern is a pattern in which light emission and non-light emission are repeated at a first time interval, and the second emission pattern is a pattern in which light emission and non-light emission are repeated at a second time interval longer than the first time interval.

8. The endoscope device according to claim 7, wherein a peak light amount of the first light is smaller than a peak light amount of the second light.

9. The endoscope device according to claim 1, wherein the second light is continuous light.

10. The endoscope device according to claim 1, further comprising:
a first light splitter configured to split the reflected light into first split light and second split light, wherein the camera head includes an image sensor that images the second split light and generates an image signal for display, and a first light receiving sensor that receives the first split light, and
the control circuit is configured to detect whether the reflected light of the third light is received by the camera head based on information of the first split light received by the first light receiving sensor.

11. The endoscope device according to claim 10, wherein the first light splitter is a half mirror that reflects the first split light to the first light receiving sensor and transmits the second split light to the image sensor.

12. The endoscope device according to claim 1, wherein the light supplied from the light source unit includes a first wavelength, and
the control circuit is configured to determine whether the first wavelength is included in the reflected light on a basis of the information of the reflected light, and determines that the light guide is connected to the insertion member when the first wavelength is included.

13. The endoscope device according to claim 12, the light supplied from the light source includes the first wavelength and a second wavelength,
the camera head includes:
a second light splitter configured to split the reflected light into fourth light including the first wavelength and fifth light including the second wavelength; and
a second light receiving sensor configured to receive the fourth light,
the camera head includes an image sensor that images the fifth light and generates an image signal for display, and
the control circuit is configured to detect whether the first wavelength is included in the reflected light based on a basis of information of the fourth light.

14. The endoscope device according to claim 13, wherein the second light splitter is a dichroic mirror that reflects the fourth light to the second light receiving sensor and transmits the fifth light to the image sensor.

15. The endoscope device according to claim 12, wherein the first wavelength is included in a wavelength range of ultraviolet rays.

16. The endoscope device according to claim 1, wherein the control circuit is configured to output information indicating a connection state between the light guide and the insertion member on a basis of a determination result.

17. The endoscope device according to claim 1, wherein a frequency of the first light is different from a frequency of ambient light that can be mixed into the insertion member.

18. The endoscope device according to claim 1, wherein the endoscope includes the light guide.

19. A connection determination method comprising:
supplying light from a light source to one end of a light guide, the light including first light that is changing in a first emission pattern with time and a second light that is at least partially superimposed on the first light and changes in a second emission pattern with time;
guiding light emitted by the light source to an insertion member to which the other end of the light guide is detachable;
emitting the light from a distal end of the insertion member to a target region of a subject;
receiving reflected light reflected by the target region and incident from the distal end of the insertion member;
detecting whether reflected light of third light changing in a combined pattern obtained by combining the first emission pattern and the second emission pattern is received on a basis of the information of the reflected light; and
determining that the light guide is connected to the insertion member when the reflected light of the third light is received.

20. The method according to claim 19, further comprising increasing a light amount of the second light supplied from the light source in response to determining that the light guide is connected to the insertion member.

21. The method according to claim 20, wherein increasing a light amount of the second light supplied from the light source in response to determining that the light guide is connected to the insertion member.

* * * * *